US010894151B2

(12) United States Patent
Ozdoganlar et al.

(10) Patent No.: US 10,894,151 B2
(45) Date of Patent: Jan. 19, 2021

(54) BIOSENSOR TATTOOS AND USES THEREFOR FOR BIOMARKER MONITORING

(71) Applicants: Carnegie Mellon University, Pittsburgh, PA (US); University of Pittsburgh—Of the Commonwealth System of Higher Education, Pittsburgh, PA (US)

(72) Inventors: O. Burak Ozdoganlar, Sewickley, PA (US); Marcel P. Bruchez, Edgewood, PA (US); Phil G. Campbell, Pittsburgh, PA (US); Jonathan W. Jarvik, Pittsburgh, PA (US); Louis Falo, Wexford, PA (US); Geza Erdos, Wexford, PA (US)

(73) Assignees: Carnegie Mellon University, Pittsburgh, PA (US); University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 441 days.

(21) Appl. No.: 15/568,327

(22) PCT Filed: Apr. 22, 2016

(86) PCT No.: PCT/US2016/028948
§ 371 (c)(1),
(2) Date: Oct. 20, 2017

(87) PCT Pub. No.: WO2016/172554
PCT Pub. Date: Oct. 27, 2016

(65) Prior Publication Data
US 2018/0119077 A1 May 3, 2018

Related U.S. Application Data

(60) Provisional application No. 62/178,954, filed on Apr. 23, 2015, provisional application No. 62/386,713, filed on Dec. 10, 2015.

(51) Int. Cl.
*A61M 37/00* (2006.01)
*A61K 49/00* (2006.01)

(52) U.S. Cl.
CPC ..... *A61M 37/0015* (2013.01); *A61K 49/0006* (2013.01); *A61K 49/0045* (2013.01); *A61K 49/0097* (2013.01); *A61M 37/0084* (2013.01); *A61M 2037/0061* (2013.01); *C12N 2750/14143* (2013.01); *C12N 2830/002* (2013.01)

(58) Field of Classification Search
CPC ........ A61M 37/0015; A61M 2037/061; A61M 37/0084; C12N 15/1086; C12N 2830/002; C12N 2750/14143; C12Q 1/66; C12Q 1/68; C12Q 2600/158; C12Q 1/6883; C12M 1/3461–1/3476; A61K 49/0006; A61K 49/0045; A61K 49/0047; A61K 49/0097

See application file for complete search history.

(56) References Cited

U.S. PATENT DOCUMENTS

| | | | |
|---|---|---|---|
| 6,093,570 A | 7/2000 | Ferrari et al. | |
| 6,458,587 B2 | 10/2002 | Ferrari et al. | |
| 6,951,758 B2 | 10/2005 | Ferrari et al. | |
| 7,439,065 B2 | 10/2008 | Ferrari et al. | |
| 8,834,423 B2 | 9/2014 | Falo, Jr. et al. | |
| 2005/0065463 A1 | 3/2005 | Tobinaga et al. | |
| 2005/0261631 A1 | 11/2005 | Clarke et al. | |
| 2011/0098651 A1 | 4/2011 | Falo, Jr. et al. | |
| 2014/0350472 A1 | 11/2014 | Falo, Jr. et al. | |
| 2015/0126923 A1 | 5/2015 | Falo, Jr. et al. | |
| 2015/0250739 A1* | 9/2015 | DeMuth ................. | C12N 15/89 424/447 |

OTHER PUBLICATIONS

Alberts et al. Rapid transcriptional assay for the expression of two distinct reporter genes by microinjection. DNA and Cell Biology, vol. 12, No. 10, pp. 935-943, 1993. (Year: 1993).*
Chosdol K., Bhagat M., Dikshit B., Madan E., Chattopadhyay P., Sinha S. (2014) Nuclear Factors Linking Cancer and Inflammation. In: Kumar R. (eds) Nuclear Signaling Pathways and Targeting Transcription in Cancer. Cancer Drug Discovery and Development. Humana Press, New York, NY, pp. 121-154. (Year: 2014).*
Swindell et al. Psoriasis drug development and GWAS interpretation through in silico analysis of transcription factor binding sites. Clinical and translational medicine. vol. 4, 13, Mar. 19, 2015, printed as pp. 1/21-3/21. (Year: 2015).*
Pusztai and Hess. Clinical trial design for microarray predictive marker discovery and assessment. Annals of Oncology, vol. 15, pp. 1731-1737, 2004. (Year: 2004).*
Mattocks et al. A standardized framework for the validation and verification of clinical molecular genetics tests. European Journal of Human Genetics, vol. 18, pp. 1276-1288, 2010. (Year: 2010).*

(Continued)

*Primary Examiner* — Jennifer Dunston
(74) *Attorney, Agent, or Firm* — The Webb Law Firm

(57) ABSTRACT

Provided herein are devices and methods used to produce tattoo biosensors that are based on spatially controlled intracutaneous gene delivery of optical reporters driven by specific transcription factor pathways for a given cytokine or other analyte. The biosensors can be specific to a given analyte, or more generically represent the convergence of several cytokines into commonly shared intracellular transcription factor pathways. These biosensors can be delivered as an array in order to monitor multiple cytokines. Biosensor redeployment can enable chronic monitoring from months to years. The tattooed biosensor array of the present invention includes endogenous reporter cells, naturally tuned to each patient's own biology and can be used to reliably measure the state of a patient in real-time.

17 Claims, 9 Drawing Sheets

Specification includes a Sequence Listing.

(56) References Cited

OTHER PUBLICATIONS

Coulman et al. Minimally invasive cutaneous delivery of macromolecules and plasmid DNA via microneedles. Current Drug Delivery, vol. 3, pp. 65-75, 2006. (Year: 2006).*
Xia et al., "In vitro- and in Vivo-Induced Transgene Expression in Human Embryonic Stem Cells and Derivatives", Stem Cells, 2008, pp. 525-533, vol. 26, No. 2.
Xiao et al., "Quantitative 3D Tracing of Gene-delivery Viral Vectors in Human Cells and Animal Tissues", Molecular Therapy, 2012, pp. 317-328, vol. 20, No. 2.
Xu et al., "Cytokine release syndrome in cancer immunotherapy with chimeric antigen receptor engineered T cells", Cancer Letters, 2014, pp. 172-178, vol. 343.
Yokota et al., "Pathogenesis of Systemic Inflammatory Diseases in Childhood: Lessons From Clinical Trials of Anti-Cytokine Monoclonal Antibodies for Kawasaki Disease, Systemic Onset Juvenile Idiopathic Arthritis, and Cryopyrin-Associated Periodic Fever Syndrome", Pediat Therapeut, 2013, pp. 1-10, vol. 3, No. 4.
Zhou et al., "Cytokine biosensors: the future of infectious disease diagnosis?", Expert Rev. Anti Infect Ther, 2012, pp. 1079-1081, vol. 10, No. 10.
Zhu et al., "Electrochemical Sensors and Biosensors Based on Nanomaterials and Nanostructures", Analytical Chemistry, 2014, pp. 230-249, vol. 87.
Allez et al., "Report of the ECCO pathogenesis workshop on anti-TNF therapy failures in inflammatory bowel diseases: Definitions, frequency and pharmacological aspects", Journal of Crohn's and Colitis, 2010, pp. 355-366, vol. 4.
Altwegg et al., "TNF Blocking Therapies and Immunomonitoring in Patients with Inflammatory Bowel Disease", Mediators of Inflammation, 2014, pp. 1-8, vol. 2014, Article ID 172821.
Al-Zahrani et al., "Microneedle-mediated vaccine delivery: Harnessing cutaneous immunobiology to improve efficacy", Expert Opin Drug Deliv., 2012, pp. 541-550, vol. 9, No. 5.
Angst et al., "Cytokine profile in human skin in response to experimental inflammation, noxious stimulation, and administration of a COX-inhibitor: A microdialysis study", Pain, 2008, pp. 15-27, vol. 139.
Aud et al., "Mechanisms of Disease: transcription factors in inflammatory arthritis", Nature Clinical Practice Rheumatology, 2006, pp. 434-442, vol. 2, No. 8.
Averbeck et al., "In situ profiling and quantification of cytokines released during ultraviolet B-induced inflammation by combining dermal microdialysis and protein microarrays", Experimental Dermatology, 2006, pp. 447-454, vol. 15.
Ayuso, "Manufacturing of recombinant adeno-associated viral vectors: new technologies are welcome", Molecular Therapy—Methods & Clinical Development, 2016, pp. 1-3, vol. 3, No. 15049.
Barton et al., "T Lymphocyte Effector Mechanisms in the Retina in Posterior Uveitis", Eye, 1994, pp. 60-65, vol. 8.
Bediz et al., "Dissolvable Microneedle Arrays for Intradermal Delivery of Biologics: Fabrication and Application", Pharm Res, 2014, pp. 117-135, vol. 31, No. 1.
Bendtzen, "Anti-TNF—a biotherapies: perspectives for evidence-based personalized medicine", Immunotherapy, 2012, pp. 1167-1179, vol. 4, No. 11.
Bendtzen et al., "Individual medicine in inflammatory bowel disease: monitoring bioavailability, pharmacokinetics and immunogenicity of anti-tumour necrosis factor-alpha antibodies", Scandinavian Journal of Gastroenterology, 2009, pp. 774-781, vol. 44, No. 7.
Bendtzen, "Personalized Medicine: Theranostics (Therapeutics Diagnostics) Essential for Rational Use of Tumor Necrosis Factor-alpha Antagonists", Discovery Medicine, 2013, pp. 201-211, vol. 15, No. 83.
Bengtson et al., "A Differential Fluorescent Receptor for Nucleic Acid Analysis", Chembiochem, 2014, pp. 228-231, vol. 15, No. 2.
Bhinge et al., "Mapping the chromosomal targets of STAT1 by Sequence Tag Analysis of Genomic Enrichment (STAGE)", Genome Research, 2007, pp. 910-916, vol. 17.
Bodenlenz et al., "Dermal PK/PD of a lipophilic topical drug in psoriatic patients by continuous intradermal membrane-free sampling", European Journal of Pharmaceutics and Biopharmaceutics, 2012, pp. 635-641, vol. 81.
Boukamp et al., "Normal Keratinization in a Spontaneously Immortalized Aneuploid Human Keratinocyte Cell Line", The Journal of Cell Biology, 1988, pp. 761-771, vol. 106.
Bryne et al., "JASPAR, the open access database of transcription factor-binding profiles: new content and tools in the 2008 update", Nucleic Acids Research, 2008, pp. D102-D106, vol. 36 (Database issue).
Campbell et al., "Tissue engineering with the aid of inkjet printers", Expert Opinion on Biological Therapy, 2007, pp. 1123-1127, vol. 7, No. 8.
Camporeale et al., "IL-6, IL-17 and STAT3: a holy trinity in auto-immunity?", Frontiers in Bioscience (Landmark Ed), 2012, pp. 2306-2326, vol. 17.
Caprioli et al., "Cytokine Therapies in Crohn's Disease: Where are We Now and where should We Go?", Inflammation & Allergy—Drug Targets, 2011, pp. 47-53, vol. 10.
Caprioli et al., "Disruption of inflammatory signals by cytokine-targeted therapies for inflammatory bowel diseases", British Journal of Pharmacology, 2012, pp. 820-828, vol. 165.
Chan et al., "Comparison of IRES and F2A-Based Locus-Specific Multicistronic Expression in Stable Mouse Lines", PLoS One, 2011, pp. 1-11, vol. 6, Issue 12.
Chen et al., "A General System for Automatic Biomedical Image Segmentation Using Intensity Neighborhoods", International Journal of Biomedical Imaging, 2011, pp. 1-13, vol. 2011.
Cheng et al., "Principles of Regulatory Information Conservation Between Mouse and Human", Nature, 2014, pp. 371-375, vol. 515, No. 7527.
Chtarto et al., "An Adeno-Associated Virus-Based Intracellular Sensor of Pathological Nuclear Factor-κB Activation for Disease-Inducible Gene Transfer", PLOS One, 2013, pp. 1-15, vol. 8, Issue 1.
Chtarto et al., "Tetracycline-inducible transgene expression mediated by a single AAV vector", Gene Therapy, 2003, pp. 84-94, vol. 10.
Cooper et al., "Inkjet-Based Biopatterning of Bone Morphogenetic Protein-2 to Spatially Control Calvarial Bone Formation", Tissue Engineering: Part A, 2010, pp. 1749-1759, vol. 6, No. 5.
Deyrieux et al., "In vitro culture conditions to study keratinocyte differentiation using the HaCaT cell line", Cytotechnology, 2007, pp. 77-83, vol. 54.
Ding et al., "Anti-Interleukin-6 Receptor Antibody Treatment in Inflammatory Autoimmune Diseases", Reviews on Recent Clinical Trials, 2006, pp. 193-200, vol. 1.
Ding et al., "Proteome-wide profiling of activated transcription factors with a concatenated tandem array of transcription factor response elements", PNAS, 2013, pp. 6771-6776, vol. 110, No. 17.
Ellis et al. "A survey of ex vivo/in vitro transduction efficiency of mammalian primary cells and cell lines with Nine natural adeno-associated virus (AAV1-9) and one engineered adeno-associated virus serotype", Virology Journal, 2013, pp. 1-10, vol. 10, No. 74.
Euskirchen et al., "Mapping of transcription factor binding regions in mammalian cells by ChIP: comparison of array- and sequencing-based technologies", Genome Research, 2007, pp. 898-909, vol. 17.
Ferguson et al., "Housekeeping proteins: A preliminary study illustrating some limitations as useful references in protein expression studies", Proteomics, 2005, pp. 566-571, vol. 5.
Filonov et al., "Bright and stable near-infrared fluorescent protein for in vivo imaging", Nat Biotechnol, 2012, pp. 757-761, vol. 29, No. 8.
Gallagher et al., "Biological response modifier therapy for refractory childhood uveitis", Br J Ophthalmol, 2007, pp. 1341-1344, vol. 91.
Gene Synthesis Handbook, Second Edition, GenScript USA, Inc., 2014.
Genovese et al., "Efficacy and safety of olokizumab in patients with rheumatoid arthritis with an inadequate response to TNF inhibitor therapy: outcomes of a randomised Phase IIb study", Ann Rheum Dis, 2014, pp. 1607-1615, vol. 73.

(56) References Cited

OTHER PUBLICATIONS

Gilmore et al., "NF-kB: where did it come from and why?", Immunological Reviews, 2012, pp. 14-35, vol. 246.
Gray et al., "Production of Recombinant Adeno-Associated Viral Vectors and Use in in Vitro and in Vivo Administration", Curr Protoc Neurosci., 2011, pp. 1-36, Chapter: Unit 4.17.
Grigorov et al., "Rapid Titration of Measles and Other Viruses: Optimization with Determination of Replication Cycle Length", PLoS One, 2011, pp. 1-12, vol. 6, No. 9.
Guo et al., "Rapid and simplified purification of recombinant adeno-associated virus", J Virol Methods, 2012, pp. 139-146, vol. 183, No. 2.
Hadam et al., "Managing risks of TNF inhibitors: An update for the internist", Cleveland Clinic Journal of Medicine, 2014, pp. 115-127, vol. 81, No. 2.
Halter et al., "Automated Live Cell Imaging of Green Fluorescent Protein Degradation in Individual Fibroblasts", Cytometry Part A, 2007, pp. 827-834, vol. 71A.
Hareendran et al., "Adeno-associated virus (AAV) vectors in gene therapy: immune challenges and strategies to circumvent them", Reviews in Medical Virology, 2013, pp. 399-413, vol. 23.
Heinz et al., "Simple combinations of lineage-determining transcription factors prime cis-regulatory elements required for macrophage and B cell identities", Mol Cell, 2010, pp. 576-589, vol. 38, No. 4.
Herberg et al., "Inkjet-based biopatterning of SDF-1beta augments BMP-2-induced repair of critical size calvarial bone defects in mice", Bone, 2014, pp. 95-103, vol. 67.
Hofmann et al., "Efficient gene transfer into human hepatocytes by baculovirus vectors", Proc. Natl. Acad. Sci. USA, 1995, pp. 10099-10103, vol. 92.
Jia et al., "Electrochemical Tattoo Biosensors for Real-Time Noninvasive Lactate Monitoring in Human Perspiration", Analytical Chemistry, 2013, pp. 6553-6560, vol. 85.
Jiang et al., "Tight regulation from a single tet-off rAAV vector as demonstrated by flow cytometry and quantitative, real-time PCR", Gene Therapy, 2004, pp. 1057-1067, vol. 11.
Jones et al., "Who Should Receive Biologic Therapy for IBD? The Rationale for the Application of a Personalized Approach", Gastroenterol Clin North Am, 2014, pp. 425-440, vol. 43.
Kang et al., "Therapeutic uses of anti-interleukin-6 receptor antibody", International Immunology, 2014, pp. 21-29, vol. 27, No. 1.
Keswani et al., "Pseudotyped Adeno-associated Viral Vector Tropism and Transduction Efficiencies in Murine Wound Healing", Wound Repair Regen, 2012, pp. 592-600, vol. 20, No. 4.
Kim et al., "Near-infrared fluorescent type II quantum dots for sentinel lymph node mapping", Nat Biotechnol, 2004, pp. 93-97, vol. 22, No. 1.
Koller, "Targeted therapy in rheumatoid arthritis", Wien Med Wochenschr, 2006, pp. 53-60, vol. 156, Nos. 1-2.
Korkmaz et al., "Therapeutic intradermal delivery of tumor necrosis factor-alpha antibodies using tip-loaded dissolvable microneedle arrays", Acta Biomaterialia, 2015, pp. 96-105, vol. 24.
Kupetsky et al., "Anti-cytokine therapy in the treatment of psoriasis", Cytokine, 2013, pp. 704-712, vol. 61.
Lallemand et al., "Reporter gene assay for the quantification of the activity and neutralizing antibody response to TNFa antagonists", Journal of Immunological Methods, 2011, pp. 229-239, vol. 373.
Lee et al., "Current concepts in the diagnosis and management of cytokine release syndrome", Blood, 2014, pp. 188-195, vol. 124, No. 2.
Mandrup-Poulsenon, "Interleukin-1 antagonists for diabetes", Expert Opinion on Investigational Drugs, 2013, pp. 965-979, vol. 22, No. 8.
Marshall et al., "Near-Infrared Fluorescence Imaging in Humans with Indocyanine Green: A Review and Update", Open Surg Oncol J., 2012, pp. 12-25, vol. 2, No. 2.
Maude et al., "Managing Cytokine Release Syndrome Associated With Novel T Cell-Engaging Therapies", Cancer J, 2014, pp. 119-122, vol. 20, No. 2.
Meglinski et al., "Quantitative assessment of skin layers absorption and skin reflectance spectra simulation in the visible and near-infrared spectral regions", Physiological Measurement, 2002, pp. 741-753, vol. 23, No. 4.
Merten et al., "Current issues in adeno-associated viral vector production", Gene Therapy, 2005, pp. S51-S61, vol. 12.
Milman et al., "Correlation of a multi-cytokine panel with clinical disease activity in patients with rheumatoid arthritis", Clinical Biochemistry, 2010, pp. 1309-1314, vol. 43.
Monaco et al., "Anti-TNF therapy: past, present and future", International Immunology, 2014, pp. 55-62, vol. 27, No. 1.
Monteleone et al., "Targets for new immunomodulation strategies in inflammatory bowel disease", Autoimmunity Reviews, 2014, pp. 11-14, vol. 13.
Morozova et al., "Far-Red Fluorescent Protein Excitable with Red Lasers for Flow Cytometry and Superresolution STED Nanoscopy", Biophysical Journal, 2010, pp. L13-L15, vol. 99.
Muller-Ladner, et al., "Role of Nuclear Factor kB in Synovial Inflammation", Current Rheumatology Reports, 2002, pp. 201-207, vol. 4.
Nograles et al., "Anti-cytokine therapies for psoriasis", Experimental Cell Research, 2011, pp. 1293-1300, vol. 317.
Papoutsaki et al., "Treatment of Psoriasis and Psoriatic Arthritis", Biodrugs, 2013, pp. 3-12, vol. 27, Suppl. 1.
Perabo et al., "Heparan Sulfate Proteoglycan Binding Properties of Adeno-Associated Virus Retargeting Mutants and Consequences for Their in Vivo Tropism", Journal of Virology, 2006, pp. 7265-7269, vol. 80, No. 14.
Piatkevich et al., "Guide to Red Fluorescent Proteins and Biosensors for Flow Cytometry", Methods Cell Biol., 2011, pp. 431-461, vol. 102.
Pras et al., "Intraocular Inflammation in Autoimmune Diseases", Seminars in Arthritis and Rheumatism, 2004, pp. 602-609, vol. 34.
Prausnitz et al., "Microneedle-based vaccines", Cliff Top Microbiol Immunol, 2009, pp. 369-393, vol. 333.
Prelog, "Vaccination in Patients with Rheumatoid Arthritis Receiving Immunotherapies", Clinical & Cellular Immunology, 2013, pp. 1-10, vol. S6.
PscAAV-MCS Expression Vector, Product Data Sheet, Cell Biolabs, Inc., San Diego, California (2015).
Qin et al., "Systematic Comparison of Constitutive Promoters and the Doxycycline-Inducible Promoter", PLoS One, 2010, pp. 1-4, vol. 5, No. 5.
Qiu et al., "The Interaction of Heparin Sulfate and Adeno-Associated Virus 2", Virology, 2000, pp. 137-147, vol. 269.
Quan et al., "Long-Term Protective Immunity from an Influenza Virus-Like Particle Vaccine Administered with a Microneedle Patch", Clinical and Vaccine Immunology, 2013, pp. 1433-1439, vol. 20, No. 9.
Reynolds et al., "Emerging immunotherapies for rheumatoid arthritis", Human Vaccines & Immunotherapeutics, 2014, pp. 822-837, vol. 10, No. 4.
Rosenbloom et al., "In vitro and in vivo protein sampling by combined microdialysis and ultrafiltration", Journal of Immunological Methods, 2006, pp. 55-68, vol. 309.
Rossi et al., "Interleukin-6 as a Therapeutic Target", Clinical Cancer Research, 2015, pp. 1248-1257, vol. 21, No. 6.
Salgo et al., "Microdialysis documents changes in the micromilieu of psoriatic plaques under continuous systemic therapy", Experimental Dermatology, 2011, pp. 130-133, vol. 20.
Sallach et al., "Tropism-modified AAV Vectors Overcome Barriers to Successful Cutaneous Therapy", Molecular Therapy, 2014, pp. 929-939, vol. 22, No. 5.
Samulski et al., "AAV-Mediated Gene Therapy for Research and Therapeutic Purposes", Annual Review of Virology, 2014, pp. 427-451, vol. 1.
Shcherbakova et al., "Near-infrared fluorescent proteins for multicolor in vivo imaging", Nat Methods, 2013, pp. 751-754, vol. 10, No. 8.
Shu et al., "Mammalian expression of infrared fluorescent proteins engineered from a bacterial phytochrome", Science, 2009, pp. 804-807, vol. 324, No. 5928.

(56) References Cited

OTHER PUBLICATIONS

Sikorski et al., "STAT1 as a central mediator of IFNy and TLR4 signal integration in vascular dysfunction", JAK-STAT, 2012, pp. 241-249, vol. 1, No. 4.

Sjogren et al., "Are Cutaneous Microdialysis Cytokine Findings Supported by End Point Biopsy Immunohistochemistry Findings?", AAPS Journal, 2010, pp. 741-749, vol. 12, No. 4.

Sjogren et al., "Cutaneous Microdialysis: Cytokine Evidence for Altered Innate Reactivity in the Skin of Psoriasis Patients?", AAPS Journal, 2012, pp. 187-195, vol. 14, No. 2.

Srivastava et al., ""Smart tattoo" Glucose Biosensors and Effect of Coencapsulated Anti-Inflammatory Agents", Journal of Diabetes Science and Technology, 2011, pp. 76-85, vol. 5, Issue 1.

Steenholdt et al., "Clinical Implications of Measuring Drug and Anti-Drug Antibodies by Different Assays When Optimizing Infliximab Treatment Failure in Crohn's Disease: Post Hoc Analysis of a Randomized Controlled Trial", The American Journal of Gastroenterology, 2014, pp. 1055-1064, vol. 109.

Steenholdt et al., "Cut-off levels and diagnostic accuracy of infliximab trough levels and antiinfliximab antibodies in Crohn's disease", Scandinavian Journal of Gastroenterology, 2011, pp. 310-318, vol. 46, No. 3.

Steenholdt, "Use of infliximab and anti-infliximab antibody measurements to evaluate and optimize efficacy and safety of infliximab maintenance therapy in Crohn's disease", Danish Medical Journal, 2013, pp. 1-24, vol. 60, No. 4.

Tanaka et al., "Image-Guided Oncologic Surgery Using Invisible Light: Completed Pre-Clinical Development for Sentinel Lymph Node Mapping", Ann Surg Oncol., 2006, pp. 1671-1681, vol. 13, No. 12.

Tincani et al., "Inflammatory molecules: a target for treatment of systemic autoimmune diseases", Autoimmunity Reviews, 2007, pp. 1-7, vol. 7.

Voorhees et al., "A phase 2 multicentre study of siltuximab, an anti-interleukin-6 monoclonal antibody, in patients with relapsed or refractory multiple myeloma", Br J Haematol, 2013, pp. 357-366, vol. 161, No. 3.

Wang et al., "Sequence features and chromatin structure around the genomic regions bound by 119 human transcription factors", Genome Research, 2012, pp. 1798-1812, vol. 22.

Wen et al., "The Role of the Transcription Factor CREB in Immune Function", J Immunol, 2010, pp. 6413-6419, vol. 185.

Wieder et al., "Optimization of Reporter Cells for Expression Profiling in a Microfluidic Device", Biomedical Microdevices, 2005, pp. 213-222, vol. 7, No. 3.

\* cited by examiner

SEQUENCE LISTING

<160> NUMBER OF SEQ ID NOS: 52

<210> SEQ ID NO 1

```
<211> LENGTH: 10
<212> TYPE: DNA
<213> ORGANISM: Homo sapiens

<400> SEQUENCE: 1
gggaatttcc                                                            10

<210> SEQ ID NO 2
<211> LENGTH: 10
<212> TYPE: DNA
<213> ORGANISM: Homo sapiens
<220> FEATURE:
<221> NAME/KEY: misc_feature
<222> LOCATION: (5)..(5)
<223> OTHER INFORMATION: n is a, c, g, or t

<400> SEQUENCE: 2 gggrnwtycc                                                            10

<210> SEQ ID NO 3
<211> LENGTH: 12
<212> TYPE: DNA
<213> ORGANISM: Homo sapiens

<400> SEQUENCE: 3
gggggaatcc cc                                                         12

<210> SEQ ID NO 4
<211> LENGTH: 10
<212> TYPE: DNA
<213> ORGANISM: Homo sapiens

<400> SEQUENCE: 4 ggggatyccc                                                            10

<210> SEQ ID NO 5
<211> LENGTH: 11
<212> TYPE: DNA
<213> ORGANISM: Homo sapiens

<400> SEQUENCE: 5
ttctgggaat t                                                          11

<210> SEQ ID NO 6
<211> LENGTH: 10
<212> TYPE: DNA
<213> ORGANISM: Homo sapiens
<220> FEATURE:
<221> NAME/KEY: misc_feature
<222> LOCATION: (6)..(6)
<223> OTHER INFORMATION: n is a, c, g, or t

<400> SEQUENCE: 6 cttccnggaa                                                            10

<210> SEQ ID NO 7
<211> LENGTH: 21
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t
```

```
<400> SEQUENCE: 7
nbbbatttcc sggaartgnn n                                              21

<210> SEQ ID NO 8
<211> LENGTH: 10
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 8 nhdnynvnhn                                                           10

<210> SEQ ID NO 9
<211> LENGTH: 14
<212> TYPE: DNA
<213> ORGANISM: Homo sapiens
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (7)..(8)
<223> OTHER INFORMATION: n is a, c, g, or t

<400> SEQUENCE: 9
rngaaannga aact                                                      14

<210> SEQ ID NO 10
<211> LENGTH: 14
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 10
natttccngg aaat                                                      14

<210> SEQ ID NO 11
<211> LENGTH: 21
<212> TYPE: DNA
<213> ORGANISM: Homo sapiens
<220> FEATURE:
<221> NAME/KEY: misc_feature
<222> LOCATION: (5)..(5)
```

```
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 11
bdhvnhttcc sggaadnrns n                                              21

<210> SEQ ID NO 12
<211> LENGTH: 14
<212> TYPE: DNA
<213> ORGANISM: Homo sapiens
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t

<400> SEQUENCE: 12
nnnttmynrk aann                                                      14

<210> SEQ ID NO 13
<211> LENGTH: 13
<212> TYPE: DNA
<213> ORGANISM: Homo sapiens

<400> SEQUENCE: 13
gaaaasygaa asy                                                       13

<210> SEQ ID NO 14
<211> LENGTH: 12
<212> TYPE: DNA
<213> ORGANISM: Homo sapiens

<400> SEQUENCE: 14
gaaagtgaaa gt                                                        12

<210> SEQ ID NO 15
<211> LENGTH: 13
<212> TYPE: DNA
<213> ORGANISM: Homo sapiens

<400> SEQUENCE: 15
saaaasygaa asy                                                       13

<210> SEQ ID NO 16
<211> LENGTH: 12
<212> TYPE: DNA
<213> ORGANISM: Homo sapiens
<220> FEATURE:
<221> NAME/KEY: misc_feature
<222> LOCATION: (12)..(12)
<223> OTHER INFORMATION: n is a, c, g, or t
```

```
<400> SEQUENCE: 16
rraavhraaa vn                                                        12

<210> SEQ ID NO 17
<211> LENGTH: 10
<212> TYPE: DNA
<213> ORGANISM: Homo sapiens

<400> SEQUENCE: 17
gtgacgtcac                                                           10

<210> SEQ ID NO 18
<211> LENGTH: 44
<212> TYPE: DNA
<213> ORGANISM: Homo sapiens

<400> SEQUENCE: 18
cgtggtcgac cacgtggtcg accacgtggt cgaccacgtg acca                     44

<210> SEQ ID NO 19
<211> LENGTH: 24
<212> TYPE: DNA
<213> ORGANISM: Homo sapiens

<400> SEQUENCE: 19
ggggaatctc ccggggaatc tccc                                           24

<210> SEQ ID NO 20
<211> LENGTH: 29
<212> TYPE: DNA
<213> ORGANISM: Homo sapiens

<400> SEQUENCE: 20
attggcgcga aataaaaatt ggcgcgaaa                                      29

<210> SEQ ID NO 21
<211> LENGTH: 16
<212> TYPE: DNA
<213> ORGANISM: Homo sapiens

<400> SEQUENCE: 21
ggttttcccg cctttt                                                    16

<210> SEQ ID NO 22
<211> LENGTH: 12
<212> TYPE: DNA
<213> ORGANISM: Homo sapiens

<400> SEQUENCE: 22
tttctctttc ag                                                        12

<210> SEQ ID NO 23
<211> LENGTH: 24
<212> TYPE: DNA
<213> ORGANISM: Homo sapiens

<400> SEQUENCE: 23
acgtggtcga ccacgtggtc gacc                                           24

<210> SEQ ID NO 24
<211> LENGTH: 10
<212> TYPE: DNA
```

<213> ORGANISM: Homo sapiens

<400> SEQUENCE: 24
gggactttcc                                                              10

<210> SEQ ID NO 25
<211> LENGTH: 32
<212> TYPE: DNA
<213> ORGANISM: Homo sapiens

<400> SEQUENCE: 25
aacatcagcc ccccacgtga tacaacatca gc                                     32

<210> SEQ ID NO 26
<211> LENGTH: 21
<212> TYPE: DNA
<213> ORGANISM: Homo sapiens

<400> SEQUENCE: 26
acatgtccca acatgttgtc g                                                 21

<210> SEQ ID NO 27
<211> LENGTH: 10
<212> TYPE: DNA
<213> ORGANISM: Homo sapiens

<400> SEQUENCE: 27
ggggcggggc                                                              10

<210> SEQ ID NO 28
<211> LENGTH: 12
<212> TYPE: DNA
<213> ORGANISM: Homo sapiens

<400> SEQUENCE: 28
ggccctgccc tc                                                           12

<210> SEQ ID NO 29
<211> LENGTH: 10
<212> TYPE: DNA
<213> ORGANISM: Homo sapiens

<400> SEQUENCE: 29
ccatatatgg                                                              10

<210> SEQ ID NO 30
<211> LENGTH: 10
<212> TYPE: DNA
<213> ORGANISM: Homo sapiens

<400> SEQUENCE: 30
ccaaatatgg                                                              10

<210> SEQ ID NO 31
<211> LENGTH: 10
<212> TYPE: DNA
<213> ORGANISM: Homo sapiens

<400> SEQUENCE: 31
attttccatt                                                              10

<210> SEQ ID NO 32
<211> LENGTH: 10

```
<212> TYPE: DNA
<213> ORGANISM: Homo sapiens
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 32 nntttccrnn                                                          10

<210> SEQ ID NO 33
<211> LENGTH: 14
<212> TYPE: DNA
<213> ORGANISM: Homo sapiens
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 33
dnnttgttta cdnb                                                     14

<210> SEQ ID NO 34
<211> LENGTH: 10
<212> TYPE: DNA
<213> ORGANISM: Homo sapiens

<400> SEQUENCE: 34
acaggaagtg                                                          10

<210> SEQ ID NO 35
<211> LENGTH: 10
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 35 ncmggawryn                                                          10

<210> SEQ ID NO 36
<211> LENGTH: 10
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 36 nvmggawryn                                                          10
```

-continued

```
<210> SEQ ID NO 37
<211> LENGTH: 12
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n is a, c, g, or t

<400> SEQUENCE: 37 ngggatttc cc                                                      12

<210> SEQ ID NO 38
<211> LENGTH: 10
<212> TYPE: DNA
<213> ORGANISM: Homo sapiens
<220> FEATURE:
<221> NAME/KEY: misc_feature
<222> LOCATION: (5)..(5)
<223> OTHER INFORMATION: n is a, c, g, or t

<400> SEQUENCE: 38 bggrntttcc                                                        10

<210> SEQ ID NO 39
<211> LENGTH: 10
<212> TYPE: DNA
<213> ORGANISM: Homo sapiens

<400> SEQUENCE: 39
ggaaattccc                                                        10

<210> SEQ ID NO 40
<211> LENGTH: 13
<212> TYPE: DNA
<213> ORGANISM: Homo sapiens

<400> SEQUENCE: 40
atttccsgga aat                                                    13

<210> SEQ ID NO 41
<211> LENGTH: 48
<212> TYPE: DNA
<213> ORGANISM: Homo sapiens

<400> SEQUENCE: 41
tcagtcagtc agtcagtcag tcagtcagtc agtcagtcag tcagtcag              48

<210> SEQ ID NO 42
<211> LENGTH: 48
<212> TYPE: DNA
<213> ORGANISM: Homo sapiens

<400> SEQUENCE: 42
ttacgtcatt acgtcattac gtcattacgt cattacgtca ttacgtca              48

<210> SEQ ID NO 43
<211> LENGTH: 42
<212> TYPE: DNA
<213> ORGANISM: Homo sapiens

<400> SEQUENCE: 43
ggtgtaaggt gtaaggtgta aggtgtaagg tgtaaggtgt aa                    42
```

<210> SEQ ID NO 44
<211> LENGTH: 36
<212> TYPE: DNA
<213> ORGANISM: Homo sapiens

<400> SEQUENCE: 44
tcgcggtcgc ggtcgcggtc gcggtcgcgg tcgcgg        36

<210> SEQ ID NO 45
<211> LENGTH: 48
<212> TYPE: DNA
<213> ORGANISM: Homo sapiens

<400> SEQUENCE: 45
tttcccgctt tcccgctttc ccgctttccc gctttcccgc tttcccgc        48

<210> SEQ ID NO 46
<211> LENGTH: 54
<212> TYPE: DNA
<213> ORGANISM: Homo sapiens

<400> SEQUENCE: 46
cacccccacc accccacca ccccaccac cccaccacc cccaccaccc ccac        54

<210> SEQ ID NO 47
<211> LENGTH: 48
<212> TYPE: DNA
<213> ORGANISM: Homo sapiens

<400> SEQUENCE: 47
tcaggtcatc aggtcatcag gtcatcaggt catcaggtca tcaggtca        48

<210> SEQ ID NO 48
<211> LENGTH: 28
<212> TYPE: DNA
<213> ORGANISM: Homo sapiens

<400> SEQUENCE: 48
tgtaatatgt aatatgtaat atgtaata        28

<210> SEQ ID NO 49
<211> LENGTH: 24
<212> TYPE: DNA
<213> ORGANISM: Homo sapiens

<400> SEQUENCE: 49
tacgtgtacg tgtacgtgta cgtg        24

<210> SEQ ID NO 50
<211> LENGTH: 48
<212> TYPE: DNA
<213> ORGANISM: Homo sapiens

<400> SEQUENCE: 50
tctagaagtc tagaagtcta gaagtctaga agtctagaag tctagaag        48

<210> SEQ ID NO 51
<211> LENGTH: 54
<212> TYPE: DNA
<213> ORGANISM: Homo sapiens

<400> SEQUENCE: 51
ggtgtaatag gtgtaatagg tgtaataggt gtaataggtg taataggtgt aata        54

```
<210> SEQ ID NO 52
<211> LENGTH: 36
<212> TYPE: DNA
<213> ORGANISM: Homo sapiens

<400> SEQUENCE: 52
aggtcaaggt caaggtcaag gtcaaggtca aggtca                              36
```

BIOSENSOR TATTOOS AND USES THEREFOR FOR BIOMARKER MONITORING

CROSS REFERENCE TO RELATED APPLICATIONS

This application is a national stage of International Patent Application No. PCT/US2016/028948 filed Apr. 22, 2016 which claims the benefit of U.S. Provisional Patent Application No. 62/178,954, filed Apr. 23, 2015, and U.S. Provisional Patent Application No. 62/386,713, filed Dec. 10, 2015, each of which is incorporated herein by reference in its entirety.

STATEMENT REGARDING FEDERALLY SPONSORED RESEARCH

This invention was made with government support under Grant No. RO1 EB012776 awarded by the National Institutes of Health. The government has certain rights in the invention.

The Sequence Listing associated with this application is filed in electronic format via EFS-Web and is hereby incorporated by reference into the specification in its entirety. The name of the text file containing the Sequence Listing is 1707310 ST25.txt. The size of the text file is 10,464 bytes, and the text file was created on Jun. 11, 2020.

BACKGROUND

The invention generally relates to biosensor tattoos that use a patient's own cells as a sensor, a device and system for precise and minimally-invasive delivery of biosensor tattoos, and uses for the device, system and biosensor tattoos for real-time monitoring of biomarkers in vivo.

Monitoring analytes, therapies, disease states and conditions is often limited to monitoring generalized clinical symptoms, therefore the direct measurement of the delivered therapy or its direct effects can only be inferred from indirect measures that are often confounded by irrelevant factors. Physiological changes often occur well before measurable symptom changes can be observed, arguing for a need for more timely biomarkers. Alternative strategies to measure the biopharmaceutical directly and its bioactivity are well-recognized as critical. More direct, and real-time measures of biomarkers will enable earlier, and more precise interventions.

Biomarkers, for example those used as a basis for clinical management of immunotherapies, require improved certified clinical assays. However, such assays involving directly monitoring the biopharmaceutical drug or its target, such as various cytokines and other biomarkers, such as inflammatory biomarkers, are not readily available in most hospitals at this time. Less common clinical assays, based on radioimmunoassay, ELISA, or homogeneous mobility shift assay formats, directly measure biomarkers or drugs, and have demonstrated a much greater precision in managing different therapies, such as immunotherapies, but take considerable time to produce results. However those assays also remain problematic, for example, because they are often based on using antibodies to identify other antibodies. Such assays are further complicated when antibodies to the active agent are elicited—a common causative factor resulting in secondary drug failure. None of these assays directly measure the bioactivity changes in the active agent's targeted cytokine. Alternative cytokine biosensing strategies are based on miniaturizing volumes for high-speed throughput microfluidic assays. Use of aptamers to replace antibody cytokine recognition suffer from similar drawbacks to traditional radioimmunoassay and ELISA formats and are unlikely candidates for in vivo cytokine biosensing. Interstitial cutaneous microdialysis sampling is an alternative approach to monitor changes in systemic cytokines, however this technique is still under development and is not compatible with either chronic deployment or in-home patient use.

A central challenge to many therapies and conditions is the lack of real-time feedback of physiological states, robustly and with precision. The state-of-the-art in monitoring biological state requires collection of biological samples (e.g, by drawing blood or interstitial fluid) and lengthy laboratory procedures that often take 24 hours or more to measure specific, (e.g. cytokine), analytes. That approach is clearly not compatible with real-time therapeutic interventions or monitoring needs. Microfluidic-based sensor systems are difficult to run continuously with biological samples due to fouling and accumulation of biological molecules over time. Multiplexed assays can measure biologically relevant levels of some cytokines, but do not measure cytokine bioactivity and are subject to assay interference. New, simple and direct sensing and monitoring approaches are therefore needed.

SUMMARY

Methods, devices, and systems for use in preparation of a tattoo biosensor (e.g., an in situ biosensor) are provided. The tattoo biosensors are based on spatially controlled intracutaneous gene delivery of optical reporters, e.g., fluorescent or colorimetric gene products, driven by specific transcription factor response elements for a given cytokine or other analyte. These biosensors can be specific to a given analyte, e.g. cytokine, or more generically representing the convergence of several analytes, e.g. cytokines, in a commonly-shared intracellular transcription factor pathway. These biosensors are delivered to the skin as an array in order to monitor one or more cytokines. In one aspect of the present invention, the deployed biosensors become active within 24-72 hours and persist for weeks, although for certain uses or conditions, more permanent cells as compared to keratinocytes, such as skin stem cells, can be targeted, resulting in a more permanent tattoo. Monthly biosensor redeployment can enable chronic monitoring from months to years. If based on colorimetric, e.g. fluorescence, optical reporter, once the biosensor is deployed, the sensor readout becomes noninvasive, using light to enable image-based detection of an analyte. Because reporter gene products are not designed for cell secretion, the risk of immune response to the biosensor is minimal.

In one aspect, recombinant Adeno-associated virus rAAV transducing particles are used to deliver the reporter gene to transfect skin cells. There is very minimal health risk with the viral-based (especially rAAV-based) biosensors. Transfection, e.g., transduction events are focused, with no secreted gene products, and transfected cells are ultimately sloughed off the skin surface. Optical-based cell reporter assays are clinically relevant as biosensor targets for the tattoo sensor array approach of described herein. Luminescent- and fluorescent-reporter based cell assays are well-established for many cytokines—targeting signal transduction pathways, specifically cytokine receptor binding, and less specifically downstream transcription factors. These gene transfection-based approaches can represent transient transfection to genomic transfection. Different condition-specific panels relevant biomarkers that can be monitored with these biosensors (see, for example and without limitation, Kang, S., et al., Therapeutic uses of anti-interleukin-6 receptor antibody. *Int Immunol*, 2015. 27(1): p. 21-29; Mandrup-Poulsen, T., et al., Interleukin-1 antagonists for diabetes. *Expert Opin Investig Drugs*, 2013. 22(8): p. 965-79; Genovese, M. C., et al., Efficacy and safety of olokizumab in patients with rheumatoid arthritis with an inadequate response to TNF inhibitor therapy: outcomes of a randomised Phase IIb study. *Ann Rheum Dis*, 2014. 73(9): p. 1607-15; Voorhees, P. M., et al., A phase 2 multicentre study of siltuximab, an anti-interleukin-6 monoclonal antibody, in patients with relapsed or refractory multiple myeloma. *Br J Haematol*, 2013. 161(3): p. 357-66; and Rossi, J. F., et al., Interleukin-6 as a Therapeutic Target. *Clin Cancer Res*, 2015). Considering immunotherapies as an example, examples of relevant biosensor targets for cytokine release syndrome (CRS) are TNF-α that is the first to become elevated with CRS onset, followed by IL-6 and IFN-γ. Reporter gene assays based on the downstream activation of transcription factors by these cytokines would respond, for example and without limitation, to increases in NF-κB, STAT3 and STAT1 activity respectively.

Use of the devices, systems and methods described herein result in a tattooed biosensor array of endogenous reporter cells, naturally tuned to each patient's own biology. The spatially-patterned tattoo biosensors based on transfection of endogenous cells, which become colorimetric, e.g. fluorescence reporters of biological markers that can be used to reliably measure the state of a patient in real-time. The methods, devices and systems described herein assure: 1) controlled and selective transfection, e.g. viral or AAV-driven transduction, of specific cells organized in distinct interpretable spatial patterns, and; 2) that the biosensor populations are optimized for reliable, high-accuracy transcription factor reporting that reflect a patient's state in a clinically-relevant fashion.

The methods, devices and systems described herein have innumerous applications, including, but not limited to monitoring of: diabetes; obesity; inflammation or any type of autoimmune diseases and conditions; pulmonary and heart diseases; infection; sepsis; biochemical warfare agents, toxins; drug development; drug dosing; drug interaction effects; allergy monitoring; systemic levels of cortisol, ions, nutrients, neurotransmitters, and mental illness treatment drugs.

BRIEF DESCRIPTION OF THE DRAWINGS

FIG. 9. AAV2 exhibits the highest transduction efficiency, in both HEK293 and HaCaT cells, of all AAV serotypes currently tested.

FIG. 11. NF-κB-responsive insert produces fluorescent reporter in response to transcription factor activation by TNF-α.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention. The term "consisting of" excludes any element, step, or ingredient not specified in the claim. As used herein, embodiments "comprising" one or more stated elements or steps also include, but are not limited to embodiments "consisting essentially of" and "consisting of" these stated elements or steps.

A "patient" is a human or animal, e.g., vertebrates or mammals, including rat, mouse, rabbit, pig, monkey, chimpanzee, cat, dog, horse, goat, guinea pig, and birds, and does not imply or require a doctor-patient or veterinarian-patient relationship.

Figure 1:
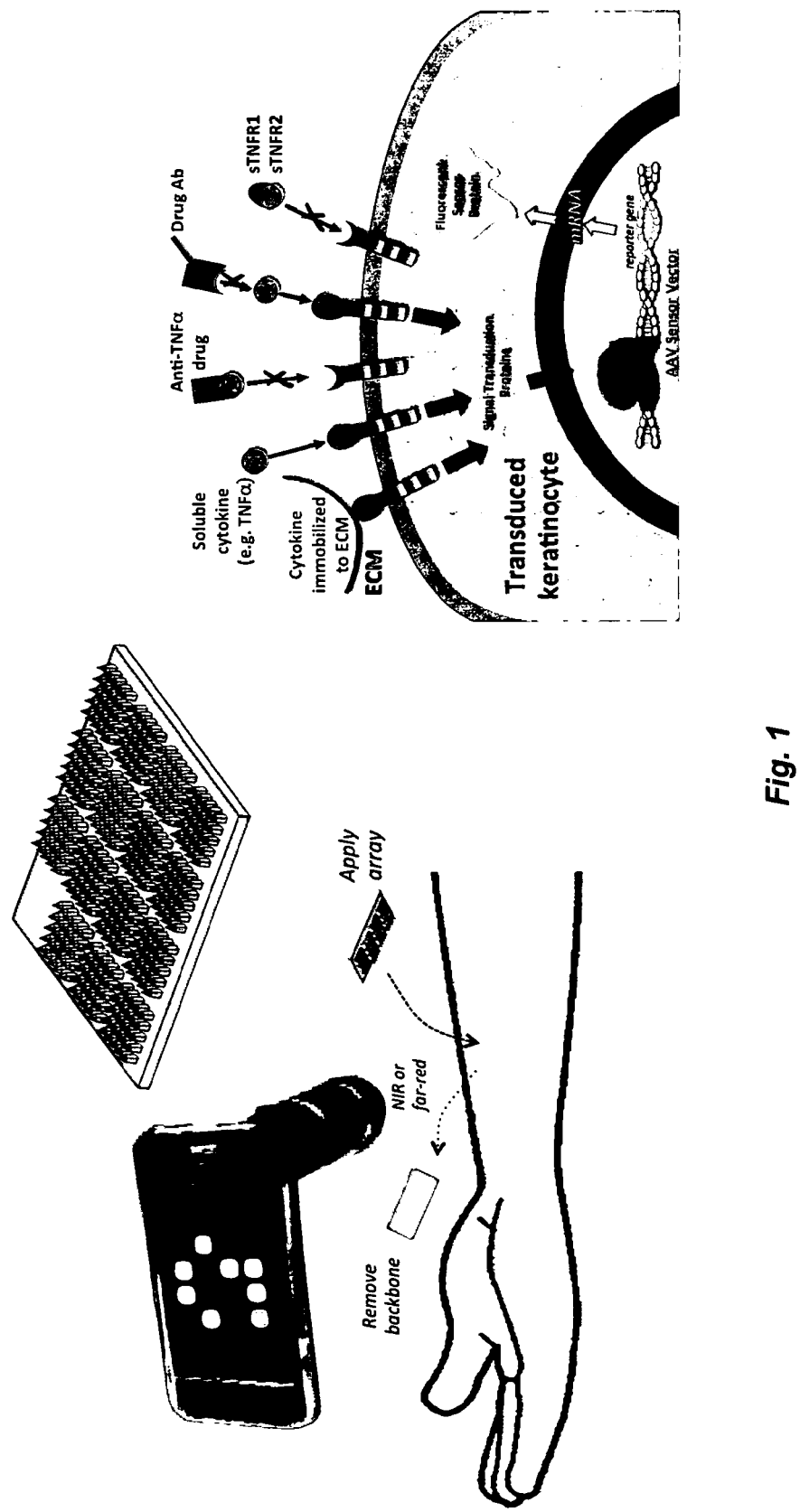
FIG. 1. Description of the approach: LEFT: The overall approach of tattoo biosensors is shown. A multi-sensor array is applied to virally transduce the cutaneous cells. The cells then turn into in-situ reporters of transcription factors, indicating the inflammation status for, e.g., up to 12 different cytokines. The result can be monitored simply by image processing the fluorescent image. The precise delivery is established by using dissolvable, tip-loaded microneedle arrays. RIGHT: The Signal transduction from the transcription factors is illustrated. The sensor cells respond by fluorescing.

Nature has perfected how to independently tune the response of cells to specific analytes, e.g. cytokines, with exquisite resolution to induce a graded cellular transcription factor response in response to the analytes in the surrounding extracellular milieu. Through binding to receptors, or otherwise influencing cells, analytes, such as cytokines, produce cellular signals that induce or suppress transcription via transcription factors within their particular response pathway. The "tattoo biosensor" approach described herein explicitly exploits this capability by converting the body's own cells into biosensors specifically designed for detecting and monitoring different diseases, conditions, and other biochemical changes in the human body. FIG. 1 provides an overview of one aspect of the methods, devices and systems described herein. The tattoo biosensors are formed in the epidermal layer of the skin where the exchange of analytes, including cytokines, between the interstitial fluid and the blood volume is typically highly effective; therefore, the extracellular cytokine milieu will reflect associated blood levels. Alternatively, the tattoo sensor can be designed to monitor local changes in skin and other tissues. According to one aspect, within the skin, keratinocytes are targeted, which are immotile cells that integrate various signaling pathways, respond robustly to challenge with various cytokines, and are eventually shed from the body. The tattoos are created in a minimally invasive fashion, e.g. in one aspect by viral (e.g., rAAV) or naked DNA (e.g., plasmid) delivery of reporter genes using dissolvable tip-loaded or layer-loaded microneedle arrays (MNAs). The tattoos utilize analyte-inducible reporter genes that produce a detectable expression product, and preferably an innately-detectable, colorimetric expression product in the presence of or absence of an analyte. By an innately-detectable colorimetric gene product, it is meant a gene product or combination of gene products, e.g. protein(s) and/or RNA(s), that produces a detectable color or signal change, e.g., wavelength and/or intensity, under physiological conditions (conditions found within the skin of a normal or individual having a disease or condition being diagnosed/monitored) without invasive or exogenous addition of a substrate and/or binding reagent, such as an antibody, e.g., directly to the tattoo. As an example, the change in levels of green-fluorescent protein, or other fluorescent proteins, are innately-detectable colorimetric proteins because they fluoresce, and thus produce a detectable signal change when exposed to electromagnetic radiation at the excitation wavelength of the protein(s). In contrast, β-galactosidase or horseradish peroxidase, though active once expressed, do not innately produce a detectable color change without exogenous addition of a particular substrate, such as X-gal (β-galactosidase) or DAB (horseradish peroxidase). It is noted that the innate color change can either be due to the presence of a colored, e.g., fluorescent gene product, or the effect of the gene product on the transduced cells by production of a colored, e.g. colored, fluorescent, or iridescent, composition from native constituents in the cell.

As an example, immune activation of signaling pathways that activate distinct transcription factors can be monitored non-invasively through the skin by a fluorescence imager and produce a quantitative, time-dependent response, effectively constituting a dynamic 2D assay barcode. This monitoring approach can be used in real time by using appropriate wearable devices, such as a watch with a fluorescence imaging underside, which continuously monitors the biological response, and optionally, processes or relays to the information as needed. Because the lifetime of epidermal keratinocytes is typically a maximum of 4 weeks, this determines the lifespan of a single application of the tattoo biosensor. Alternatively, more permanent skin cell populations (e.g. epidermal stem cells of the stratum basale) can be stably transfected so as to produce a lifetime-permanent sensor.

By primarily targeting keratinocytes, virally-driven transduced reporter cells are expected to function for approximately 28 days, or can be made into permanent reporters (e.g. by targeting epithelial stem cells). Alternatively, for chronic feedback, sensors can be reapplied in neighboring anatomic locations since the tattoos are easy to apply. There are innumerous applications for this in-situ, real-time tattoo biosensors, including (but not limited to): diabetes: to monitor blood levels of insulin, glucose, glucagon and other metabolic balance levels; obesity: Monitor metabolic indicators, such as glucose, leptin, ghrelin, glucagon; inflammation: to monitor inflammation state (systemic or local) in real time, this is applied to any type of autoimmune diseases and conditions; pulmonary and heart diseases: to monitor changes in blood pH levels; infection; biochemical warfare agents; toxins, drug development: feedback during the drug development stage, whether on humans or rodents or any other model; drug dosing: accurate drug dosing through patient specific and real time monitoring-monitoring drug response or drug metabolites; drug interaction effects; allergy monitoring, allergens and histamines; and systemic levels of cortisol, ions, nutrients, neurotransmitters, mental illness treatment drugs, etc.

The terms "transfect", "transfection", "transfected", and like terms refer to the introduction of a gene into a eukaryotic cell, such as a keratinocyte, and includes "transduction," which is viral-mediated gene transfer, for example, by use of recombinant AAV, adenovirus (Ad), lentiviral, or any other applicable viral-mediated gene transfer platform.

According to one aspect, an in vivo, robust, non-invasive biosensor array ('tattoo' biosensors) composed of virally-activated endogenous cutaneous cells is provided for monitoring biomarkers in real-time. The cell-based biosensors virally transduce skin cells to transform them into cell reporters that provides real-time feedback of systemic or local conditions (disease, inflammation, drug levels, etc.) by fluorescing in response to the bioactivity of targeted biomarkers. Dissolvable microneedle arrays (MNAs), which incorporate the viral vectors (sensor drivers) in their tips, or at defined levels (positions, in terms of distance from the backing) along their shafts, are used for precise, easy-to-deploy, and pain-free intradermal delivery to target specific cells (e.g., keratinocytes) and form defined arrayed patterns of different biomarker reporters and/or calibration-standard vectors. A transgenic, non-human animal, a transgenic, non-human vertebrate, and a transgenic, non-human mammal, such as a transgenic rat, mouse, rabbit, pig, monkey, chimpanzee, cat, dog, horse, goat, guinea pig, or bird are provided. By transgenic, it is meant that the organism contains one or more exogenous (non-native) genes artificially introduced into its cells, such as its keratinocytes, fibroblasts or skin stem cells. In the context of the present invention, cells of the non-human animal, vertebrate, mammal, rat, mouse, rabbit, pig, monkey, chimpanzee, cat, dog, horse, goat, guinea pig, or bird comprise one or more artificially-introduced reporter genes as described herein as a tattoo.

Optionally, active agents and/or excipients are co-delivered with the transfecting materials or transducing particles carrying the reporter gene for any suitable purpose, for example for co-delivery of effective amounts of agents for subsiding (reducing) initial inflammation associated with needle (stab) wounds or for further promoting transduction, as needed. Active agents for reducing wound-induced inflammation include effective amounts of: antihistamines such as brompheniramine, buclizine, chlorpheniramine, cinnarizine, clemastine, cyclizine, cyproheptadine, diphenhydramine, diphenylpyraline, doxylamine, meclozine, pheniramine, promethazine, triprolidine, acrivastine, astemizole, cetirizine, desloratadine, fexofenadine, levocetirizine, loratadine, mizolastine, terfenadine, a pharmaceutically acceptable salt thereof, or a combination thereof; including chlorpheniramine maleate, diphenhydramine hydrochloride, doxylamine succinate, cetirizine hydrochloride, fexofenadine hydrochloride, hydroxyzine hydrochloride, loratidine or a combination thereof, anti-inflammatory agents, such as steroidal anti-inflammatory agents or non-steroidal anti-inflammatory agents, such as nabumetone, tiaramide, proquazone, bufexamac, flumizole, epirazole, tinoridine, timegadine, dapsone, aspirin, diflunisal, benorylate, fosfosal, diclofenac, alclofenac, fenclofenac, etodolac, indomethacin, sulindac, tometin, fentiazac, tilomisole, carprofen, fenbufen, flurbiprofen, ketoprofen, oxaprozin, suprofen, tiaprofenic acid, ibuprofen, naproxen, fenoprofen, indoprofen, pirprofen, flufenamic, mefenamic, meclofenamic, niflumic, oxyphenbutazone, phenylbutazone, apazone and feprazone, piroxicam, sudoxicam, isoxicam and tenoxicam, and pharmaceutically acceptable salts thereof, and combinations thereof, and/or imunosuppressants, such as cyclosporine, tacrolimus, and methotrexate.

According to one aspect of the invention, viral transduction, (e.g., adenoviral-associated virus (AAV)-directed transduction) is used to target native keratinocytes to create biosensors that report changes in cell signaling transcription factors (transcription factors) as biomarkers of physiological state due to a disease, condition, drug, environmental exposure, etc. Changes in transcription factor activity are non-invasively detected from colorimetric reporter, e.g. fluorescent protein, expression and interpreted, e.g., using image processing techniques.

Therefore, provided herein according to one aspect of the invention is a microneedle array comprising: a backing that can be rigid or flexible; and a plurality of microneedles attached to a side of the backing. The microneedles comprise one or more nucleic acids comprising a first gene encoding a colorimetric protein under transcriptional control of a vertebrate transcription factor-responsive element (TRE) such that when transfected into a vertebrate cell, the gene is expressed differently in the presence of a vertebrate transcription factor that binds the TRE than in the absence of the transcription factor and the difference in expression of the gene is optically detectable (that is, detectable either visually, or by imaging skin and analyzing the image, e.g., by a computer method, to detect differences in color intensity of the transfected cell at one or more wavelengths). In one aspect, the plurality of microneedles comprise either at one location, or at discrete, addressable locations on the backing a nucleic acid or a plurality of different nucleic acids, with the nucleic acid or each of the plurality of different nucleic acids comprising a gene encoding a colorimetric protein, wherein the nucleic acid or a first nucleic acid of the plurality of different nucleic acids comprises a first gene encoding a colorimetric protein under transcriptional control of a vertebrate transcription factor-responsive element such that when transfected into a vertebrate cell, the gene is expressed differently in the presence of a vertebrate transcription factor than in the absence of the transcription factor and the difference in expression of the gene is optically detectable, that is either visually or by imaging, optionally with a computer-implemented process for analysis of the image data. When present, a second, different nucleic acid of the plurality of different nucleic acids comprises a second gene encoding a colorimetric protein that is the same or different than the colorimetric protein of the first gene, under different transcriptional control than the first gene. When more than one nucleic acids is present, in order to differentially measure transcription from the different reporter genes, the colorimetric protein gene products are either detectably different, e.g. they have detectably-different colors, permitting use of different imaging wavelengths to distinguish co-localized reporters, and in the case of fluorescent reporters, they have different excitation and/or emission wavelengths, and preferably both, or if the reporters are located at discrete, addressable positions in the microneedle array, and therefore in the biosensor tattoo, they can be the same or different colorimetric proteins.

The backing and microneedles of the microneedle array form a unitary structure, in that the microneedles are physically attached to, and protrude from one side of the backing in substantially a single direction, such that the plurality of microneedles can be simultaneously introduced into the skin by pressing the microneedle array into the skin of a patient using an applicator device, such as a spring-loaded applicator, as are known in the art. Alternatively, the application can be done manually by pressing the microneedle array into skin by hand. The backing is any useful substrate of any suitable shape and composition, to which the microneedles are attached, and is optionally configured to fit into an applicator, such as a spring-loaded microneedle applicator. In one aspect, for larger arrays, the backing is flexible, permitting conformation of the array to curved body surfaces. The microneedles carry the nucleic acid, and unless the nucleic acid (e.g. contained in a recombinant virus particle) is absorbed or adsorbed to a surface of the microneedle, it is contained within the microneedle, for instance integrated into or within a dissolvable or bioerodible polymeric constituent of the microneedle. The microneedle array optionally comprises multiple, different nucleic acids, e.g. recombinant virus particles or plasmids, in discrete microneedles at discrete, addressable locations in the microneedle array, such that different nucleic acids are deposited at discrete, addressable locations on the skin of a patient.

In one aspect, two or more different nucleic acids are provided on the microarray, each nucleic acid comprising a reporter gene under different transcriptional control, and either contained in the same microneedle, or in different microneedles that are spatially-separated and addressable. When the two different nucleic acids are contained in the same microneedle, they produce colorimetric proteins that are distinguishable in terms of color, or in the case of fluorescent proteins, in terms of excitation and/or emission wavelength. In this case, the different colorimetric proteins are not spatially-separated, but are separately-addressable. When the two different nucleic acids are contained in separate, discrete, addressable microneedles, the colorimetric protein produced by the gene contained in the nucleic acid can be the same or different.

In the context of the microneedle array, the array comprises a plurality of different nucleic acids. In one aspect, the nucleic acids are naked DNA, such as a plasmid, or another suitable nucleic acid or analog thereof and the microneedle containing the naked DNA also optionally contains a transfection reagent, as are broadly-known, that enhances transfection of skin cells with the naked DNA. The nucleic acids are optionally conjugated to a protein or other composition that facilitates transfection of skin cells with the nucleic acid. The nucleic acids are optionally contained within a nanoparticle dispersed within a dissolvable or bioerodible portion of the microneedle, where the nanoparticle comprises a composition that facilitates transfection of skin cells with the nucleic acid. The nucleic acids are optionally, and preferably in many instances, recombinant, packaged viral genomes (nucleic acid that can be packaged into a viral particle), such that the nucleic acid is part of a transduction particle by which a cell can be transfected, as is broadly-known, for example as described in detail below regarding rAAV technologies.

AAV (adeno-associated virus), is a virus belonging to the genus *Dependoparvovirus*, and family Parvoviridae. The virus is a small replication-defective, non-enveloped virus. AAV is not currently known to cause any disease by itself. AAV requires a helper virus, such as adenovirus or herpes simplex virus, to facilitate productive infection and replication. In the absence of helper virus, AAVs establish a latent infection within the cell, either by site-specific integration into the host genome or by persisting in episomal forms. Gene therapy vectors using AAV can infect both dividing and quiescent cells. Furthermore, AAV serotypes have different tropism and can infect cells of multiple diverse tissue types. While eleven serotypes of AAV have been identified to date, AAV2 was among the first to be identified and has been consistently used for the generation of recombinant AAV vectors.

The AAV virion shell is approximately 25 nm in diameter and encapsulates a single-stranded DNA genome that consists of two large open reading frames (ORFs) flanked by inverted terminal repeats (ITR). The ITRs are the only cis-acting elements required for genome replication and packaging. In wild-type AAV, the left ORF encodes four replication proteins responsible for site-specific integration, nicking, and helicase activity, as well as regulation of promoters within the AAV genome. AAV possesses a 4.7 kb genome, and as such, efficient packaging of recombinant AAV (rAAV) vectors can be performed with constructs ranging from 4.1 kb to 4.9 kb in size (See, e.g., Samulski, R J, et al., AAV-Mediated Gene Therapy for Research and Therapeutic Purposes, *Annu. Rev. Virol.* 2014. 1:427-51).

Helper-free production of the rAAV requires transfection of the following components into host cells, typically 293 cells (HEK293 cells), which are broadly available, or similar cell lines: (1) an rAAV vector containing the transgene expression cassette flanked by the two ITRs, (2) expression of Rep and Cap proteins, typically provided by a helper plasmid in trans, and (3) adenovirus genes encoding E1, E2A, E4, and virus-associated RNA, also provided, at least in part by another helper plasmid in trans (293 cells produce the Ad E1 gene in trans). Rep and Cap proteins, which are necessary for viral packaging, are replication proteins and capsid proteins, respectively. Rep proteins consist of rep 78, 68, 52 and 40. They specifically are involved with the replication of AAV. Cap proteins are comprised of three proteins, VP1, VP2 and VP3, with molecular weight of 87, 72 and 62 kDa, respectively. These capsid proteins assemble into a near-spherical protein shell of 60 subunits. Helper-free AAV packaging systems are broadly available, for example from Clontech of Mountain View, Calif., from Cell Biolabs, Inc. of San Diego, Calif., and see, e.g., U.S. Pat. Nos. 6,093,570, 6,458,587, 6,951,758, and 7,439,065. In scAAV (self-complementary AAV), the right ITR contains a deletion of D-sequence (the packaging signal) and a terminal resolution site mutation ($\Delta$trs), which prevent Rep-mediated nicking and force packaging of dimer or self-complementary genomes (see FIG. 8). Making dsAAV from scAAV vector renders much improved transduction both in vitro and in vivo (see, e.g., pscAAV-MCS Expression vector, Product Data Sheet, Cell Biolabs, Inc., San Diego, Calif. (2015)).

Preparation of rAAV transducing particles, such as scAAV transducing particles is routine. Since the transfection method is often considered unsuitable for large-scale production, the infection of cell lines stably expressing Rep and Cap with adenovirus carrying a vector genome has afforded the ability to scale-up. Another option includes infection of proviral cell lines with adenovirus or herpes simplex virus vector carrying an AAV Rep and Cap expression cassette. These methods still require the complete elimination of adenovirus (or herpesvirus) during the production process. However, in baculovirus expression vector systems for rAAV vector production in insect SF9 cells, the components of AAV production, including Rep and Cap proteins, as well as vector genomes are provided by separate recombinant baculoviruses. Ayuso, E., "Manufacturing of recombinant adeno-associated viral vectors: new technologies are welcome", *Molecular Therapy—Methods & Clinical Development* (2016) 3, 15049; doi:10.1038/mtm.2015.49, and Merten, O-W, et al., describe numerous robust current rAAV production methods, though commercial scale-up and validation needs improvement. High viral titers ($\sim 10^{12}$-$10^{1}$' vp/mL) may be required for certain uses described herein. Protocols are available in the literature for concentration and purification of AAV vectors, allowing production of virus at these high concentrations (see, e.g., Gray S J, et al. (2011) Production of recombinant adeno-associated viral vectors and use in in vitro and in vivo administration. *Curr Protoc Neurosci.* doi:10.1002/

0471142301.ns0417s57 and Guo P, et al. (2012) Rapid and simplified purification of recombinant adeno-associated virus. *J Viral Methods* 183(2):139-146).

Once the virus has been produced in the, e.g., 293 cells, the cells are collected, lysed, and the resultant virus is purified. Density gradient ultracentrifugation, e.g., in cesium chloride or nonionic iodixanol (VISIPAQ™) gradients and column chromatography, such as ion-exchange, heparin-affinity, or mucin-affinity column chromatography, depending on the AAV serotype. Once the rAAV has been purified and concentrated to a suitable concentration, the virus can be used for in vitro cell transduction or for in vivo animal injection at an appropriate MOI (Multiplicity of Infection).

Numerous rAAV vectors have been made containing genes for expressing fluorescent proteins, and are commercially available. A "gene" is a genetic element for production of a gene product such as a protein or RNA. A gene for production of a protein product includes, from 5' to 3' according to convention: one or more regulatory elements (transcription control elements) such as promoters, transcription response elements (TREs), repressors, enhancers; an open-reading frame (ORF) encoding a protein or a sequence encoding a functional RNA; and a polyadenylation (pA) site. Due to size limitations, genes for use in rAAV vectors typically do not include introns. rAAV vectors also include the 5' ITR and 3' ITR flanking the gene, which is referred to as a transgene. Thus a typical rAAV genome has the following structure, in order from 5' to 3' on the sense strand: ITR-promoter-transgene ORF-pA-ITR, and in one aspect of the present invention, the promoter includes a TRE and the transgene ORF is that of a colorimetric, e.g., fluorescent protein. Methods of molecular cloning of rAAV transgene constructs, preparation of rAAV particles, and storage and use thereof are broadly-known and further technical details are unnecessary for one of ordinary skill in the art to be able to construct useful rAAV vectors, and produce and use rAAV particles as described herein. As indicated above, so long as the gene sequence is less than the packaging limit of rAAV or scAAV, it is useful for production of a transduction particle as described herein.

AAV is but one of many robust and well-characterized viral vectors suited for gene therapy, which also includes, without limitation, gammaretroviruses, lentiviruses, adenovirus, and herpes simplex virus. While AAV is likely preferred in many instances, other safe and effective viral transducing particles can be developed based on the inducible colorimetric genes described herein for use in the devices, systems and methods described herein. Likewise, plasmid or naked DNA, optionally combined with transfection reagents in the microneedles described herein also are expected to be useful. Nevertheless, the high efficiency transduction of safe, recombinant viral particles, such as rAAV particles, are preferred in many instances.

By "expression" or "gene expression," it is meant the overall flow of information from a gene (without limitation, a functional genetic unit for producing a gene product, such as RNA or a protein in a cell, or other expression system encoded on a nucleic acid and comprising: a transcriptional control sequence, such as a promoter and other cis-acting elements, such as transcriptional response elements (TREs) and/or enhancers; an expressed sequence that typically encodes a protein (referred to as an open-reading frame or ORF) or functional/structural RNA, and a polyadenylation sequence), to produce a gene product (typically a protein, optionally post-translationally modified or a functional/ structural RNA). By "expression of genes under transcriptional control of," or alternately "subject to control by," a designated sequence such as TRE or transcription control element, it is meant gene expression from a gene containing the designated sequence operably linked (functionally attached, typically in cis) to the gene. A gene that is "under transcriptional control" of a TRE or transcription control element, is a gene that is transcribed at detectably different levels in the presence of a transcription factor, such as, for example, NF-κB, CREB, STAT1, or STAT3, as further described below, and in the context of the present disclosure, produces a detectable difference in transcription levels as a result of increased or decreased production of a colorimetric protein. The designated sequence may be all or part of the transcriptional control elements (without limitation, promoters, TREs, enhancers and response elements), and may wholly or partially regulate and/or affect transcription of a gene. A "gene for expression of" a stated gene product is a gene capable of expressing that stated gene product when placed in a suitable environment—that is, for example, when transformed, transfected, transduced, etc. into a cell, and subjected to suitable conditions for expression. In the case of a constitutive promoter "suitable conditions" means that the gene typically need only be introduced into a host cell. In the case of an inducible promoter, "suitable conditions" means when factors that regulate transcription, such as DNA-binding proteins, are present or absent—for example an amount of the respective inducer is available to the expression system (e.g., cell), or factors causing suppression of a gene are unavailable or displaced—effective to cause expression of the gene.

A "reporter gene" is a gene that comprises an open-reading frame encoding a protein or nucleic acid that is innately-detectable, e.g., colored or fluorescent, and, in the case of an inducible gene, a transcriptional control element that controls expression of the gene depending on the amount of a specific analyte present. The transcriptional control element includes promoters, enhancers, transcription factor-responsive elements (TREs, e.g., transcription factor binding sequences), suppressors, etc., as are broadly-known. As an example, an exemplary NF-κB transcriptional response element includes a plurality of NF-κB (nuclear factor κB) transcription factor response elements (e.g. four) 5' to a minimal cytomegalovirus promoter, as is broadly known in the art. The transcriptional control element is placed in the reporter gene construct 5' to a colorimetric protein, e.g. a fluorescent, protein, such as GFP, thereby causing expression of the colorimetric protein. Additional control elements, such as a WPRE (woodchuck hepatitis virus post-transcriptional regulatory element) which can increase expression from certain viral vectors, can be included in the construct.

In one aspect, a transcription control element that is responsive to physiological or metabolic activity directly or indirectly sensitive to an increased or decreased production of an analyte comprises a suitable transcriptional promoter and transcriptional response elements (TREs). A common number of public and private databases provide specific and/or consensus sequences of TREs, such as the TRANSFAC® professional or nonprofessional databases (BIOBASE, Waltham, Mass.), the JASPAR database (Bryne J C, et al., JASPAR, the open access database of transcription factor-binding profiles: new content and tools in the 2008 update, *Nucleic Acids Res.* 2008 January; 36(Database issue):D102-6), ChIPBase, Factorbook (Wang, J., et al., Sequence features and chromatin structure around the genomic regions bound by 119 human transcription factors. *Genome Research* 2012 22 (9), 1798-1812), and Salk ChipSeq (Homer Motif, Heinz S, et al. Simple Combinations of Lineage-Determining Transcription Factors Prime cis-Regulatory Elements Required for Macrophage and B Cell Identities. *Mol Cell* 2010 May 28; 38(4):576-589), among others.

Exemplary TREs include (R=A/G, Y=CT, S=G/C, W=A/T, K=G/T, M=A/C, B=C/G/T, D=A/G/T, H=A/C/T, V=A/C/G, and N=any base):

NF-κB:
(SEQ. ID NO: 1)
GGGAATTTCC
(consensus sequence is GGGRNWTYCC, SEQ ID NO: 2), or (SEQ ID NO: 3)
GGGGGAATCCCC,
or (SEQ ID NO: 4)
GGGGATYCCC;

- STAT3 (Signal transducer and activator of transcription 3): TTCTGGGAATT (from Santa Cruz Biotechnology) (SEQ ID NO: 5), CTTCCNGGAA (SEQ ID NO: 6), NBBBATTTCCSGGAARTGNNN (SEQ ID NO: 7), or NHDNYNVNHN (SEQ ID NO: 8),
- STAT1 (Signal transducer and activator of transcription 1): when activated by IFN-gamma, it binds to GAS sequences along with STAT3 (many possible sequences; TTCCCCGAA comes from the promoter for IRF-1, so might be interesting for crosstalk analysis). STAT1 also binds to ISRE (interferon-sensitive response element) sequences (consensus sequence RNGAAANNGAAACT) (SEQ ID NO: 9), NATTTCCNGGAAAT (SEQ ID NO: 10), BDHVNHTTCCSGGAADNRNSN (SEQ ID NO: 11), or NNNTTMYNRKAANN (SEQ ID NO: 12);
- CREB (cAMP response element binding protein): binds to the cAMP response element, canonically TGACGTCA; and
- IRF1 (interferon-regulatory factor 1): binds to the IRF-E consensus sequence, consensus G(A)AAASYGAAASY (SEQ ID NO: 13), GAAAGTGAAAGT (SEQ ID NO: 14), SAAAASYGAAASY (SEQ ID NO: 15), or RRAAVHRAAAVN (SEQ ID NO: 16).

Table 1 provides additional exemplary TREs.

TABLE 1

| Transcriptional Factor | Recognition Element |
| --- | --- |
| AP-1 (activator protein 1) | (TCAGTCAG)6 (SEQ ID NO: 41) |
| C/EBPalpha | (TTACGTCA)6 (SEQ ID NO: 42) |
| c-Fos | (GGTGTAA)6 (SEQ ID NO: 43) |
| c-Jun | (GTGACGTCAC)6 (SEQ ID NO: 17) |
| c-Myc | (CGTGGTCGACCACGTGGTCGACCACGTGGTCGACCACGTGACCA)2 (SEQ ID NO: 18) |
| c-Rel | (GGGGAATCTCCCGGGGAATCTCCC)3 (SEQ ID NO: 19) |

TABLE 1 -continued

| Transcriptional Factor | Recognition Element |
| --- | --- |
| DP-1 | (ATTGGCGCGAAATAAAAATTGGCGCGAAA)2 (SEQ ID NO: 20) |
| E2F+p107 | (TCGCGG)6 (SEQ ID NO: 44) |
| E2F-1 | (TTTCCCGC)6 (SEQ ID NO: 45) |
| E2F-4/DP-2 | (GGTTTTCCCGCCTTTT)4 (SEQ ID NO: 21) |
| Egr-1 | (CACCCCCAC)6 (SEQ ID NO: 46) |
| ErbA | (TCAGGTCA)6 (SEQ ID NO: 47) |
| FosB | (TGTAATA)4 (SEQ ID NO: 48) |
| HIF-1 (Hypoxia-inducible factor 1) | (TACGTG)4 (SEQ ID NO: 49) |
| HSF1 | (TCTAGAAG)6 (SEQ ID NO: 50) |
| INF | (TTTCTCTTTCAG)5 (SEQ ID NO: 22) |
| JunD | (GGTGTAATA)6 (SEQ ID NO: 51) |
| Max1 | (ACGTGGTCGACCACGTGGTCGACC)3 (SEQ ID NO: 23) |
| NF-κB | (GGGACTTTCC)4 (SEQ ID NO: 24) |
| N-Myc | (AACATCAGCCCCCCACGTGATACAACATCAGC)2 (SEQ ID NO: 25) |
| p53 | (ACATGTCCCAACATGTTGTCG)8 (SEQ ID NO: 26) |
| REVERB-alpha | (AGGTCA)6 (SEQ ID NO: 52) |
| Sp1 | (GGGGCGGGGC)6 (SEQ ID NO: 27) |
| Sp3 | (GGCCCTGCCCTC)3 (SEQ ID NO: 28) |
| SRF | (CCATATATGG)3 (SEQ ID NO: 29) |
| YY1 | (CCAAATATGG)4 (SEQ ID NO: 30) |
| NFAT (Nuclear factor of activated T-cells) | ATTTTCCATT (SEQ ID NO: 31) NNTTTCCRNN (SEQ ID NO: 32) TTTCCDN (NFAT2) |
| FOXO1 (Forkhead box protein O1) | CTGTTTAC DNNTTGTTTACDNB (SEQ ID NO: 33) NTGYTKHY |
| ETS-1 (V-Ets Avian Erythroblastosis Virus E26 Oncogene Homolog 1) | ACAGGAAGTG (SEQ ID NO: 34) NCMGGAWRYN (SEQ ID NO: 35) NVMGGAWRYN (SEQ ID NO: 36) |
| RELA (p65) | NGGGGATTTCCC (SEQ ID NO: 37) BGGRNTTTCC (SEQ ID NO: 38) GGAAATTCCC (SEQ ID NO: 39) |

TABLE 1 -continued

| Transcriptional Factor | Recognition Element |
|---|---|
| STAT 1/2 (STAT1:2 heterodimers) | ATTTCCSGGAAAT (SEQ ID NO: 40) |

Although these are human sequences and consensus sequences, there is conservation among species and many TRE sequences that function in human cells will also be expected to do so in mice, or any mammal or vertebrate.

Production of useful nucleic acid constructs, such as recombinant viral vectors for production of colorimetric proteins under constitutive transcriptional control, or under transcriptional control of a TRE, is routine, in that molecular cloning procedures are routine. Further, a number of companies can custom-synthesize and verify multi-kilobase genes, making the production of reporter genes or genomes as described herein, such as rAAV or scAAV genomes, routine.

A colorimetric reporter gene expresses a colorimetric protein that either: fluoresces as a fluorophore; is colored under any applicable illumination; or produces a detectable color change in cells containing the reporter (e.g., by causing production of a colored substance, such as a melanin) without exogenous addition of a substrate to a cell, tissue or organism expressing the gene, hence, the protein is "innately colorimetric". For uses in vivo, far-red, and near-infrared proteins may be favored due to their ability to be detected in tissue. However, because the described biosensor tattoo is on the skin, and therefore is essentially superficial, other colors, such as fluorescent red, green, yellow, cyan, etc., will prove useful. A large variety of colorimetric proteins, including nucleic acid constructs containing genes for expressing, and/or ORFs encoding a broad spectrum of colorimetric proteins, with a wide variety of excitation and emission spectra in the case of fluorescent protein are known and are available. Sequences of such genes are and ORFs are broadly-available either freely or commercially, e.g., from Addgene, Clontech, Evrogen, and DNA 2.0, among many others. An exemplary, and non-limiting list of far-red, and near-infrared fluorescent proteins include: eqFP578, Katushka, mKate, mNeptune, e2-Crimson, TagRFP657, mCardinal, iRFP670, iRFP682, iRFP702, iRFP(iRFP713), iRFP720, iSplit, PAiRFP1, PAiRFP2, mCherry, tdTomato, DsRed-Monomer, dsRed-Express2, dsRed-Express, dsRed2, RFP, asRed2, mStrawberry, mRuby, mApple, jRed, HcRed1, mRaspberry, dKeima-Tandem, mPlum, AQ143, mIFP, iFP1.4, iFP2.0, or NirFP (See, e.g., Morozova, K. S., et al., Far-red fluorescent protein excitable with red lasers for flow cytometry and superresolution STED nanoscopy. *Biophys J*, 2010. 99(2): p. L13-5); 2) those that bind an endogenous chromophore and convert it to a fluorescent state, including the biliverdin binding proteins like IFP1.4 and other bacterial phytochrome binding proteins (BphPs) (Filonov, G. S., et al., Bright and stable near-infrared fluorescent protein for in vivo imaging. *Nat Biotechnol*, 2011. 29(8): p. 757-61; Shcherbakova, D. M., et al., Near-infrared fluorescent proteins for multicolor in vivo imaging. *Nat Methods*, 2013. 10(8): p. 751-4; Shu, X., et al., Mammalian expression of infrared fluorescent proteins engineered from a bacterial phytochrome. *Science*, 2009. 324(5928): p. 804-7; and Piatkevich, et al., Guide to Red Fluorescent Proteins and Biosensors for Flow Cytometry. *Methods Cell Biol.* 2011; 102: 431-461). Although red, far-red, and near-infra-red-emitting proteins are preferred for imaging in deeper tissues, due to the surface (skin) expression of the colorimetric proteins, other potentially, exemplary useful fluorescent proteins include proteins that emit at different wavelengths, e.g., in the green, yellow, and cyan wavelengths, such as GFP (green fluorescent protein), YFP (yellow fluorescent protein), or CFP (cyan fluorescent protein), or any equivalent thereof are broadly-known and are available. These fluorescent proteins function as reporters allowing for easy identification, detection, and/or tracking of expression of the transgene. Sequences encoding a large variety of fluorescent proteins, including those listed herein, and plasmid and viral constructs containing those sequences, e.g., as part of a gene, are broadly, publically available (e.g., in GenBank, UniProt, Addgene, etc.), and need not be recited herein.

In one aspect, the microneedle array according to the present invention comprises in discrete, addressable, e.g. spatially separated needles or clusters of needles, independently, one or more nucleic acids comprising colorimetric reporter genes under control of different transcription control elements, e.g. TREs, independently selected from one or more, e.g. 1, 2, 3, 4, 5, 6, 7, 8, 9, 10 or more of AP-1 TRE, C/EBPalpha TRE, c-Fos TRE, c-Jun TRE, c-Myc TRE, c-Rel TRE, DP-1 TRE, E2F+p107 TRE, E2F-1 TRE, E2F-4/DP-2 TRE, Egr-1 TRE, ErbA TRE, FosB TRE, HIF-1 TRE, HSF1 TRE, INF TRE, JunD TRE, Max1 TRE, NF-κB TRE, N-Myc TRE, p53 TRE, REVERB-alpha TRE, Sp1 TRE, Sp3 TRE, SRF TRE, YY1 TRE, NFAT TRE, FOXO1 TRE, ETS-1 TRE, RELA TRE, STAT1 TRE, STAT2 TRE, STAT1/2 TRE, STAT3 TRE, CREB TRE, IRF1 TRE, and/or SRC-1 TRE, optionally NF-κB TRE, a CREB TRE, a STAT1 TRE, a STAT3 TRE, a STAT 1/2 heterodimer TRE, an IRF1 TRE, an NFAT TRE, a FOXO1 TRE, an ETS1 TRE, an AP-1 TRE, an HIF-1 TRE, an ETS-1 TRE, or a RELA TRE, and optionally from NF-κB TRE, a CREB TRE, a STAT1 TRE, a STAT3 TRE, a STAT 1/2 heterodimer TRE, an IRF1 TRE, an NFAT TRE, a FOXO1 TRE, an ETS1 TRE, an AP-1 TRE, an HIF-1 TRE, an ETS-1 TRE, or a RELA TRE.

A variety of microneedle arrays are useful in the devices, systems, and methods described herein. Microneedle arrays can be prepared, for example, from metals, polymers, polysaccharides, and/or ceramics, and can have any shape or configuration useful for dermal administration of nucleic acids as described herein. Microneedle arrays comprise a backing or substrate and a plurality of microneedles attached thereto, with bioactive agents, for example, adsorbed to, absorbed to, or integrated within the microneedles. In an alternative embodiment, the tattoo biosensors are administered by use of a dermal roller microneedle device, and the nucleic acids are introduced by applying or patterning the nucleic acids on skin treated with the dermal roller. Although this is a possible method of delivery of the nucleic acids, it is unlikely to provide the levels of transfection or the precision of delivery location that a microneedle device containing the nucleic acids would provide.

Figure 2:
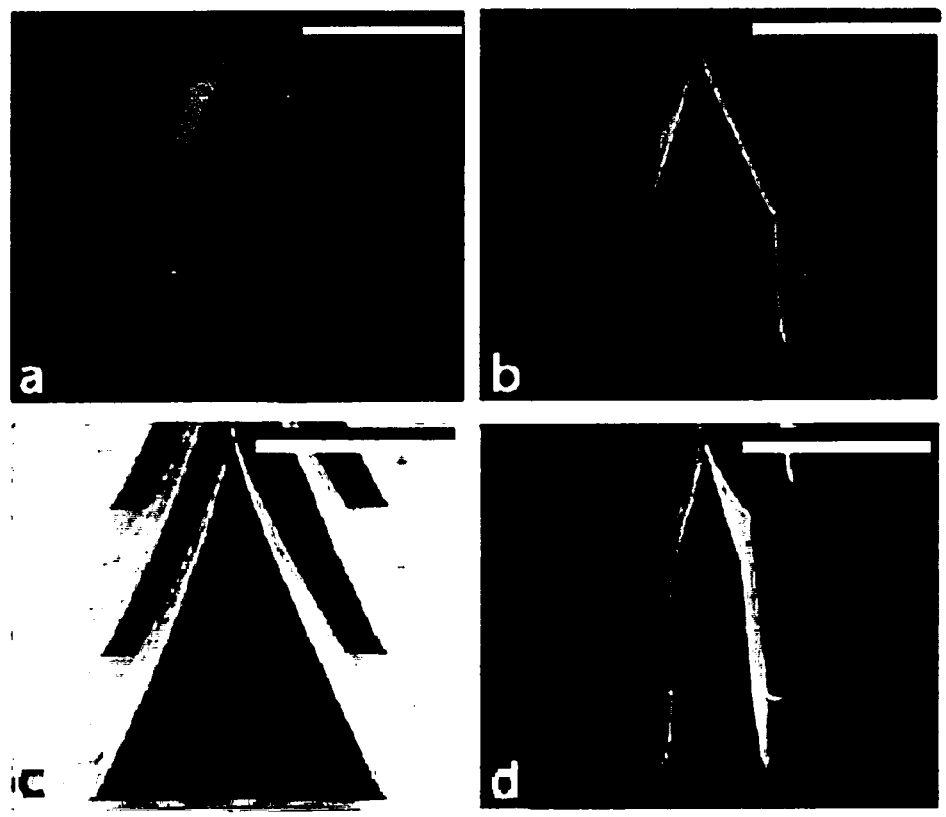
FIG. 2. Photomicrographs of microneedle arrays (MNAs) with diverse geometries and from a myriad of materials: (a) Bevel shape d CMC MNA, (b) Bevel-shape CMC/Trehalose MNA, (c) Pyramid PVP MNA and (d) Obelisk shape CMC/PVP MNA.

United States Patent Publication Nos. 2011/0098651; 2014/0350472; 2015/0126923, and U.S. Pat. No. 8,834,423, describe certain exemplary microneedle arrays and methods of making and using microneedle arrays. As an example, apparatuses and methods are described for fabricating dissolvable microneedle arrays using master molds formed by micromilling techniques. For example, microneedle arrays can be fabricated based on a mastermold (positive) to production mold (negative) to array (positive) methodology. Micromilling technology can be used to generate various micro-scale geometries on virtually any type of material, including metal, polymer, and ceramic parts. Micromilled mastermolds of various shapes and configurations can be effectively used to generate multiple identical female production molds. The female production molds can then be used to microcast various microneedle arrays. Direct micromilling of mastermolds can replace other exemplary microneedle array production methods that involve expensive, complex and equipment-sensitive SU-8 based lithography or laser etching techniques, which are conventionally used to create mastermolds for dissolvable needle arrays. In addition, as discussed below, micromilling can provide for the construction of more complex mastermold features than can conventional lithography and laser etching processes. Precision-micromilling systems can be used for fabricating a microneedle mastermold, using micro-scale (for example, as small as 10 µm (micrometers or microns)) milling tools within precision computer controlled miniature machine-tool platforms. The system can include a microscope to view the surface of the workpiece that is being cut by the micro-tool. The micro-tool can be rotated at ultra-high speeds (200,000 rpm) to cut the workpiece to create the desired shapes (FIG. 2). Micromilling process can be used to create complex geometric features with many kinds of material, which are not possible using conventional lithographic or laser etching processes. Various types of tooling can be used in the micromilling process, including, for example, carbide micro-tools or diamond tools.

Mastermolds can be micromilled from various materials, including, for example, Cirlex® (DuPont, Kapton® polyimide). Mastermolds can be used to fabricate flexible production molds from a suitable material, such as a silicone elastomer, e.g., SYLGARD® 184 (Dow Corning). The mastermold is desirably formed of a material that is capable of being reused so that a single mastermold can be repeatedly used to fabricate a large number of production molds. Similarly each production mold is desirably able to fabricate multiple microneedle arrays.

In one example, production molds are made from SYLGARD® 184 (Dow Corning), and are mixed at a 10:1 SYLGARD® to curing agent ratio. The mixture is degassed for about 10 minutes and poured over the mastermold to form an approximately 8 mm layer, subsequently degassed again for about 30 minutes and cured at 85° C. for 45 minutes. After cooling down to room temperature, the mastermold is separated from the cured silicone, and the silicone production mold is trimmed. From a single mastermold, a large number of production molds (e.g., 100 or more) can be produced with very little, if any, apparent deterioration of the Cirlex® or acrylic mastermolds.

In one example, to construct the microneedle arrays, a base material is used to form portions of each microneedle that have bioactive components and portions that do not. Of course, if desired, each microneedle can comprise only portions that contain bioactive components; however, to control the delivery of the bioactive component(s) and to control the cost of the microneedle arrays, each microneedle optionally is constructed such that a portion of the structure has a bioactive component and a portion does not include a bioactive component. Variations in the size, shape and number of the microneedles, and location of the bioactive component(s) in the microneedles, may be readily varied by varying the mastermold, or by varying the deposition and patterning of the materials used to produce the microarray.

A large variety of materials useful for preparation of the microneedle array are available, along with variation in the location of such materials in the microarray. Precise positioning and layering of the materials during, e.g., spin casting, of the microneedle array will yield any desired structure. For example, in one aspect, the microneedle array, both base and needles, are manufactured from a single carrier composition including a dissolvable composition and a bioactive agent, such as a reporter gene, such as rAAV transducing particles. The "carrier composition" is one or more dissolvable and/or bioerodible compounds or compositions into which a bioactive agent is mixed, and in the context of the present disclosure forms a structure with physical parameters, and lack of negative effects on the bioactive agent as used herein, including sufficient safety to a patient, such that the carrier composition is useful as a component of the microneedles and microneedle arrays described herein.

In another aspect, the needle tips are prepared from a carrier composition, such as a rapidly-dissolving composition, containing the reporter gene, and the backing and portions of the microneedles between the backing and the needle tip are prepared from the same or a different composition as compared to the carrier composition, such as a polymer, that does not necessarily dissolve, and is free from the reporter gene present in the needle tips. In yet a further aspect, a microneedle array is provided, where the microneedles have needle tips comprising a dissolvable composition that do not contain the reporter gene or that contains a bioactive agent (e.g. drug, drug product, biological, active agent, etc.), such as an anti-inflammatory composition such as an antihistamine or NSAID (non-steroidal anti-inflammatory drug) as are broadly known. A second layer of the needle between the needle tip and the backing contains a carrier composition with the reporter gene, e.g., the rAAV transducing particles as described herein, and the backing and optionally a portion of the needles between the second layer and the backing are prepared from a different composition that optionally comprises a bioactive agent. In describing the various layers of the microneedles, unless specifically indicated, the recitation of the relative location of layers do not imply direct contact between the layer, such that additional unspecified layers may be located between recited layers. Nevertheless, recitation of structures also implies and includes in various aspects direct contact between layers described.

In various aspects the microneedle device comprises a plurality of needles comprising dissolvable or bioerodible compositions comprising a bioactive agent and one or more additional layers of the needle that optionally comprise a different bioactive agent, and a backing to which the microneedles are attached. In yet a further aspect, a layer of the microneedles between a layer containing the reporter gene is prepared from a rapidly-dissolving composition, such as a saccharide, or other composition that dissolves faster than the layer containing the reporter gene, such that the backing is rapidly released from the microneedles upon administration to a patient, and the positions of the microneedles containing the reported gene remain in the skin of the patient to release the reporter genes and any additional bioactive agent(s) at any time frame ranging from minutes, to hours or even days, depending on the rate of dissolution and where pertinent, bioerosion of the carrier composition in situ.

Materials useful for the various layers of the microneedle are broadly-known. The compositions comprising the rAAV transducing particles or a cell transfection composition comprising a reporter gene as described herein, such as recombinant virus particles or other effective transfection reagents and the reporter gene, comprise a dissolvable composition, e.g. a bioerodible composition. A dissolvable composition is one that solubilizes under microneedle array injection conditions either directly or is first degraded through the action of native enzymatic or chemical processes, such as by hydrolysis. Rapidly-degrading compositions, such as saccharides, e.g., polysaccharides or polysaccharide gums, e.g. carboxymethylcellulose (CMC), that can be dried or cured to produce useful microneedles, are particularly useful, as they not only can pierce the skin, but dissolve within seconds or minutes. Other polymers (e.g., copolymers) are useful for preparation of microneedle arrays, including polyester copolymers such as poly(lactic-co-glycolic acid) (PLGA). However, other compositions can be used, for example mixtures of copolymer compositions and saccharides in a single composition. As would be appreciated by those of skill in the art the preceding merely provides illustrative examples of different materials and possible variations of the microneedle array structure, e.g., layering of different compositions, and patterning of different reporter genes. Although in the figures herein, patterns are shown as rectangular or square grids, any shape, pattern, layout, etc. of the microneedles will be suitable for the devices, systems and methods described herein—so long as different nucleic acids are physically located in microneedles at discrete, addressable locations that can be visually or optically detected and distinguished.

In one aspect, CMC is generally preferable to PLGA as the base material of the microneedle arrays described herein. The PLGA based devices can limit drug delivery and vaccine applications due to the relatively high temperature (e.g., 135° C. or higher) and vacuum required for fabrication. In contrast, a CMC-based matrix can be formed at room temperature in a simple spin-casting and drying process, making CMC-microneedle arrays more desirable for incorporation of sensitive biologics, peptides, proteins, nucleic acids, and other various bioactive components. In one example, CMC-hydrogel is prepared from low viscosity sodium salt of CMC with or without active components (as described below) in sterile $dH_2O$. In the exemplary embodiment, CMC can be mixed with sterile distilled water ($dH_2O$) and with the active components to achieve about 25 wt % CMC concentration. The resulting mixture is stirred to homogeneity and equilibrated at about 4° C. for 24 hours. During this period, the CMC and any other components can be hydrated and a hydrogel can be formed. The hydrogel is degassed in a vacuum for about an hour and centrifuged at about 20,000 g for an hour to remove residual micro-sized air bubbles that might interfere with a spincasting/drying process of the CMC-microneedle arrays. The dry matter content of the hydrogel can be tested by drying a fraction (10 g) of it at 85° C. for about 72 hours. The ready-to-use CMC-hydrogel is desirably stored at about 4° C. until use.

When present, active components, such as viral particles, are incorporated in a hydrogel of CMC at a relatively high (e.g., up to 20-30%) CMC-dry biologics weight ratio before the spin-casting process. Arrays can be spin-cast at room temperature, making the process compatible with the functional stability of a structurally broad range of bioactive components. Since the master and production molds can be reusable for a large number of fabrication cycles, the fabrication costs can be greatly reduced. The resulting dehydrated CMC-microneedle arrays are generally stable at room temperature or slightly lower temperatures (such as about 4° C.), and preserve the activity of the incorporated biologics, facilitating easy, low cost storage and distribution.

In another aspect, the MNA includes microneedles that are not dissolvable, but that include the transfecting materials/transducing particles coated thereon, or contained within a lumen or via thereof, which also allows for access to skin cells.

Expression of the reporter genes described herein are said to be optically or visibly detectable, in that they are either detectable visually, that is, by eye, or detectable using imaging devices such as cameras or other imaging sensors, or scanners, optionally in conjunction with a light emitter, such as an LED (light-emitting diode) or an OLED (organic light-emitting diode), for example to illuminate the tattoo at an excitation wavelength of a fluorescent reporter protein as described herein. Optical detection devices include camera sensors, such as charge-coupled devices (CCDs), or complementary metal-oxide-semiconductor (CMOS) devices, as are broadly-known, though any imaging or scanning sensor can be used in order to generate a digital representation of the tattoo either under visible light or illuminated by a light source. Once image data is obtained, it is analyzed using image-analysis software, to determine color changes, e.g. intensity and/or wavelength shift, as is appropriate at each addressable location on a patient's skin.

More specifically, in one aspect the illumination and detection of the biosensor tattoo is performed by a device comprising, emitters such as LEDs or OLEDs that produce light at an excitation wavelength of the colorimetric proteins. The device additionally comprises an imaging sensor, such as a CCD or CMOS sensor. Further, the device comprises a processor, data storage, computer-implemented instructions implemented by the processor for storing image data obtained from the imaging sensor in the data storage, and, optionally, one or more sets of computer-implemented instructions for analyzing the data to produce an output relating to expression levels of at least the first gene. Methods and devices provided herein allow for transmitting data to and from the device, and/or outputting the image data and/or information produced by analysis of the image data. Additionally provided herein, optionally, is a wireless or wired communication module for transmitting data from the device to and optionally from a compute, and optionally, a display for providing output produced by the computer-implemented instructions.

Figure 3:
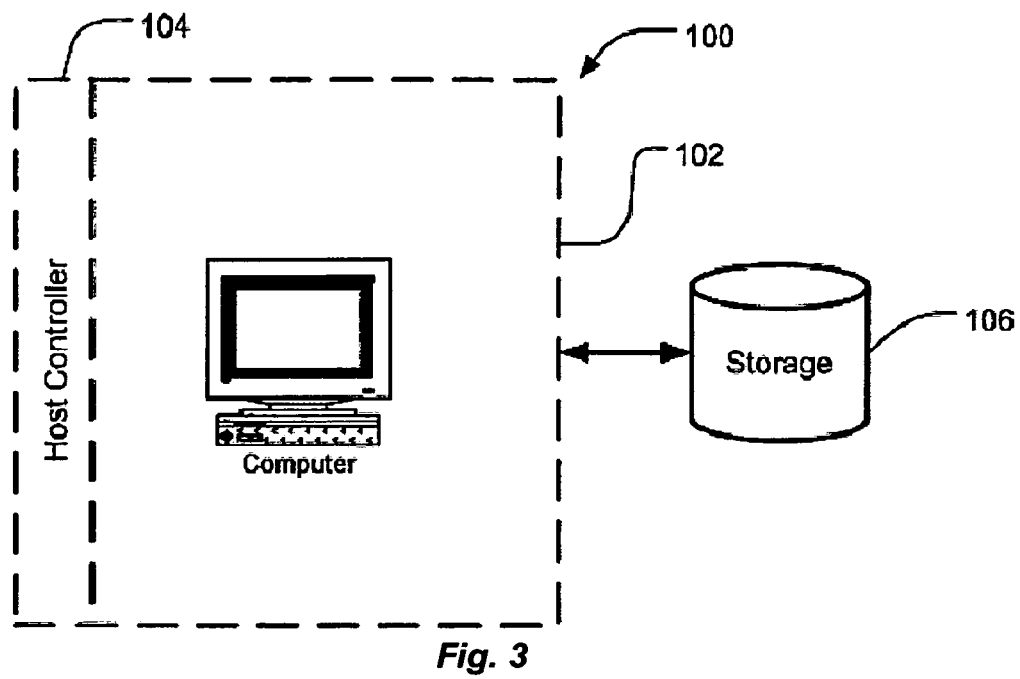
FIG. 3. A schematic of a computer system.

In one aspect, a computer is used to obtain and analyze image data. Image data analysis methods are implemented on a computing device (computer) as processes. In the context of computing, a process is, broadly speaking any computer-implemented activity that generates an outcome, such as implementation of a mathematical or logical formula or operation, algorithm, etc. and is executed by instructions processed by a processor. FIG. 3 illustrates one embodiment of a system 100 for implementing computer-implemented methods. The system 100 may include a device 102 operating under the command of a controller 104. Device 102 may be referred to herein, without limitation, as a computer or computing device. The broken lines are intended to indicate that in some implementations, the controller 104, or portions thereof considered collectively, may instruct one or more elements of the device 102 to operate as described. Accordingly, the functions associated with the computer-implemented methods (e.g., processes, software, programs) described herein may be implemented as software executing in the system 100 and controlling one or more elements thereof. An example of a device 102 in accordance with one embodiment of the present invention is a general-purpose computer capable of responding to and executing instructions in a defined manner. Other examples include a special-purpose computer including, for example, a personal computer (PC), a credit card-sized-computer such as a Raspberry Pi or Arduino, a workstation, a server, a laptop computer, a smart device, such as a smartphone or smartwatch, a web-enabled telephone, a web-enabled personal digital assistant (PDA), a microprocessor, an integrated circuit, an application-specific integrated circuit, a microprocessor, a microcontroller, a network server, a Java™ virtual machine, a logic array, a programmable logic array, a micro-computer, a mini-computer, or a large frame computer, or any other component, machine, tool, equipment, or some combination thereof capable of responding to and executing instructions.

In one non-limiting aspect, system 100 is implemented as a smart device, such as a smartphone or smartwatch, including Windows, iOS, or Android-based systems. Furthermore, the system 100 may include a central processing engine including a baseline processor, memory, and communications capabilities. The system 100 also may include a communications system bus to enable multiple processors to communicate with each other. In addition, the system 100 may include storage 106 in the form of computer readable medium/media, such as a disk drive, optical drive, a tape drive, flash memory (e.g., a non-volatile computer storage chip), cartridge drive, and control elements for loading new software. In various aspects, one or more reference values may be stored in a memory associated with the device 102. Data, such as images obtained and/or produced by the devices, methods and systems described herein may be organized non-transiently on computer readable media in a database, which is an organized collection of data for one or more purposes, usually in digital form Aspects of the controller 104 may include, for example, a program, code, a set of instructions, or some combination thereof, executable by the device 102 for independently or collectively instructing the device 102 to interact and operate as programmed, referred to herein as "programming instructions". One example of a controller 104 is a software application (for example, operating system, browser application, client application, server application, proxy application, on-line service provider application, and/or private network application) installed on the device 102 for directing execution of instructions. In one embodiment, the controller 104 may be a Windows, iOS, or Android, based operating system. The controller 104 may be implemented by utilizing any suitable computer language (e.g., C\C++, UNIX SHELL SCRIPT, PERL, JAVA™, JAVASCRIPT, HTML/DHTML/XML, FLASH, WINDOWS NT, UNIX/LINUX, APACHE, RDBMS including ORACLE, INFORMIX, and MySQL) and/or object-oriented techniques.

In one aspect, the controller 104 may be embodied permanently or temporarily in any type of machine, component, physical or virtual equipment, storage medium, or propagated signal capable of delivering instructions to the device 102. In particular, the controller 104 (e.g., software application, and/or computer program) may be stored on any suitable computer readable media (e.g., disk, device, or propagated signal), readable by the device 102, such that if the device 102 reads the storage medium, the functions described herein are performed. For example, in one embodiment, the controller 104 may be embodied in various computer-readable media for performing the functions associated with processes embodying the modeling methods. Communication is wired or wireless, and is implemented by any applicable hardware and software, and includes, for example, near-field (NFC), Wi-Fi, LAN, and cellular protocols and devices, such as, for illustrative purposes only: Bluetooth 4.0, Zigbee (IEEE 802.15.4), IEEE 802.11, Ethernet, and GSM protocols.

The following examples are provided for illustrative purposes.

Example 1: Design and Construction of Viral Reporters

Robust in vivo compatible reporter constructs are developed that can be delivered into skin cells to report noninvasively on changes in gene expression in living skin. This reporter is selected from available fluorescent proteins, selected for optimal brightness in the cellular context, low toxicity on overexpression, and the rate of turnover of the protein in cells. These reporters are put into effective AAV viruses for intradermal delivery, and optimized for their ability to transduce cultured keratinocytes. A set of virally-expressed housekeeping constructs that express this reporter protein at varying levels are used for internal calibration. Tet-inducible and tet-repressible reporter constructs are generated to provide an exogenously controlled reporter-gene assay that can function for validation of cellular arrays both in vitro and in vivo. Using the viral vectors for the reference reporters and the Tet-controlled reporters, arrays of cellular reporters are constructed that may be used for reporting purposes under various conditions, for example by virally transducing keratinocytes in culture in each well of a multi-well plate with distinct viruses, establishing an in-vitro model of the in situ cellular array that functions within skin, and providing the required components for in vivo validation. Inflammation dependent transcription factor reporter gene assays are prepared under transcriptional control of NF-κB, STAT1, STAT3 and CREB TREs. The fluorescent reporter proteins that are employed, preferably have high expression levels (without toxicity), high fluorescence efficiency, high brightness, and emission in the spectral range that is compatible with through-skin imaging. The reporters require addition of nothing to the cell other than the reporter construct itself to function. Fluorescent proteins, including visible, far-red and infrared fluorescent proteins are utilized. These come in two categories: 1) those that form a chromophore directly in the protein structure, basically intrinsically fluorescent proteins and their red-red-shifted versions, including far-red proteins like TagRFP657. These proteins all can be excited with wide-field violet to far-red light, and emit fluorescence that is readily detected through 1 mm of skin, the maximum implantation depth expected.

Transducing particles can be produced at very high titers, and capsid sequence variants are available that give high transduction efficiencies in cultured keratinocytes and in keratinocytes in the skin (Sallach, J., et al., Tropism-modified AAV vectors overcome barriers to successful cutaneous therapy. *Mol Ther,* 2014. 22(5): p. 929-39). AAV also elicits limited immunogenicity in the human and no immune response in rodents, and variants with highly attenuated responses in humans have been identified.

Figure 4:
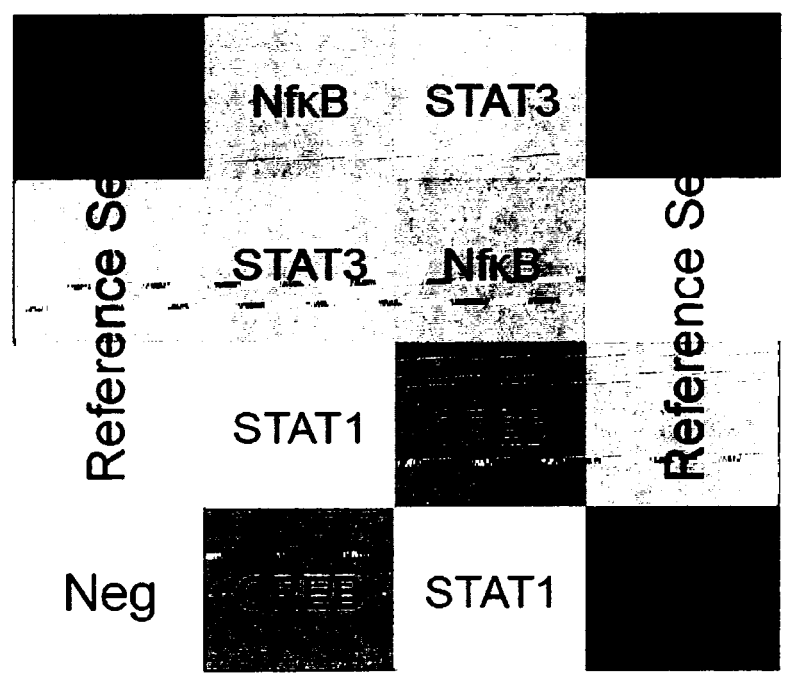
FIG. 4. Panel design for a 4-plex sensor array with in-array quantitative references and orientation design.

For each potential protein reporter, a reporter gene-containing AAV genome construct is prepared by broadly-known molecular cloning methods, or be de novo synthesis. The construct comprises a reporter gene, including a transcription control element, e.g., promoter, operably linked to an ORF encoding the reporter protein, and including all required AAV sequences necessary for packaging, transfer and transduction of a cell by the particle to express the reporter gene, including ITR sequences flanking the reporter gene. Viruses are used in the tattoo sensor at defined reference points, and optionally as quantitative calibration standards, where reporter genes having different expression levels are encoded at precise array locations. An exemplary layout is shown in FIG. 4, for an inflammation-specific array, with each square representing a cluster of microneedles including an AAV reporter (a recombinant AAV transducing particle containing a nucleic acid comprising a colorimetric reporter gene) under transcriptional control of the specified STAT1, STAT3, CREB, and NF-κB TREs. Reference sensors are under transcriptional control of constitutive or housekeeping gene promoters.

Gene expression and protein expression experiments are typically compared to a reference "housekeeping" gene that is ubiquitously expressed in the cell and usually expressed at a constant level. Transcriptional control elements of housekeeping standards include actin, tubulin, GAPDH, vinculin, cyclophilin B, cofilin, Lamin B1, HSP60, CoxIV, PCNA and others (Ferguson, R. E., et al., Housekeeping proteins: a preliminary study illustrating some limitations as useful references in protein expression studies. *Proteomics*, 2005. 5(2): p. 566-71). The promoter and/or enhancer regions of these genes and other constitutive promoters for mammalian expression (see, e.g., Qin, J. Y., et al., Systematic comparison of constitutive promoters and the doxycycline-inducible promoter. *PLoS One*, 2010. 5(5): p. e10611) are used to construct the reference sensors using a colorimetric protein as described herein Example 2: Patterned Intradermal Delivery of AAV Reporters Using Layer-Loaded Dissolvable Microneedle Arrays Here, a minimally invasive intradermal delivery approach is provided for the AAV-based reporter genes (reporters) using layer-loaded dissolvable microneedle arrays (LL-dMNAs), such as tip-loaded dissolvable microneedle arrays (TL-dMNAs). Layer-loading refers to creation of a layer comprising the reporter genes, with layers being spaced at a distance from the backing, whether at the tip of the microneedles, or as a layer between the tip and the backing at a distance from the backing. The tattoo biosensing approach for inflammation assessment relies on efficient, precise, and reproducible administration of AAV-based sensor-drivers to the relevant skin microenvironments. The unique advantages of dissolvable MNAs support their use for effective, precise, reproducible, and patterned intradermal delivery of AVV-based sensor-drivers. Optimal and clinically relevant LL-dMNAs designs (including material) balance the trade-offs among manufacturability, survivability (transduction efficiency), longevity, mechanical performance (penetration without failure), intradermal release profile, and delivery precision. An example of useful microfabrication technology for producing dissolvable MNAs with uniformly encapsulated biocargo is described above. Different microneedle and array designs and different dissolvable materials can be used for encapsulating AAV reporters. Exemplary materials are described above and herein.

Figure 5:
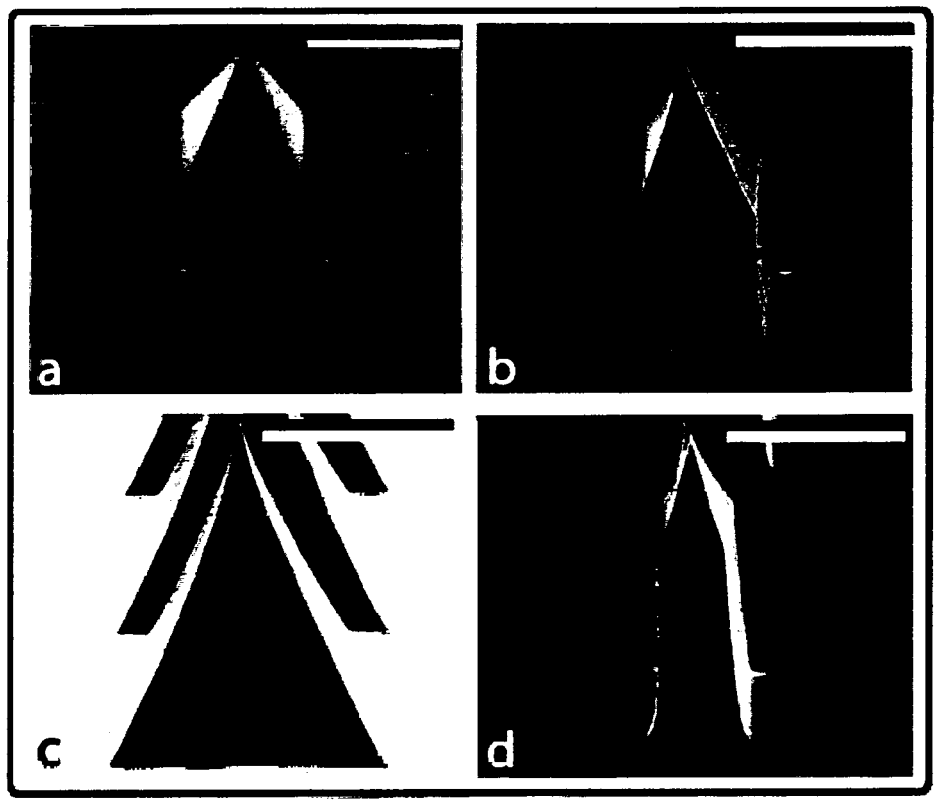
FIG. 5. MNAs with diverse geometries and from a myriad of materials: (a) Bevel shape d CMC MNA, (b) Bevel-shape CMC/Trehalose MNA, (c) Pyramid PVP MNA and (d) Obelisk shape CMC/PVP MNA.

As indicated above, the micromilling, micromolding and spin-casting approach is highly effective to reproducibly fabricate dissolvable LL-MNAs with unique microneedle and array geometries (see FIG. 5).

Figure 6:
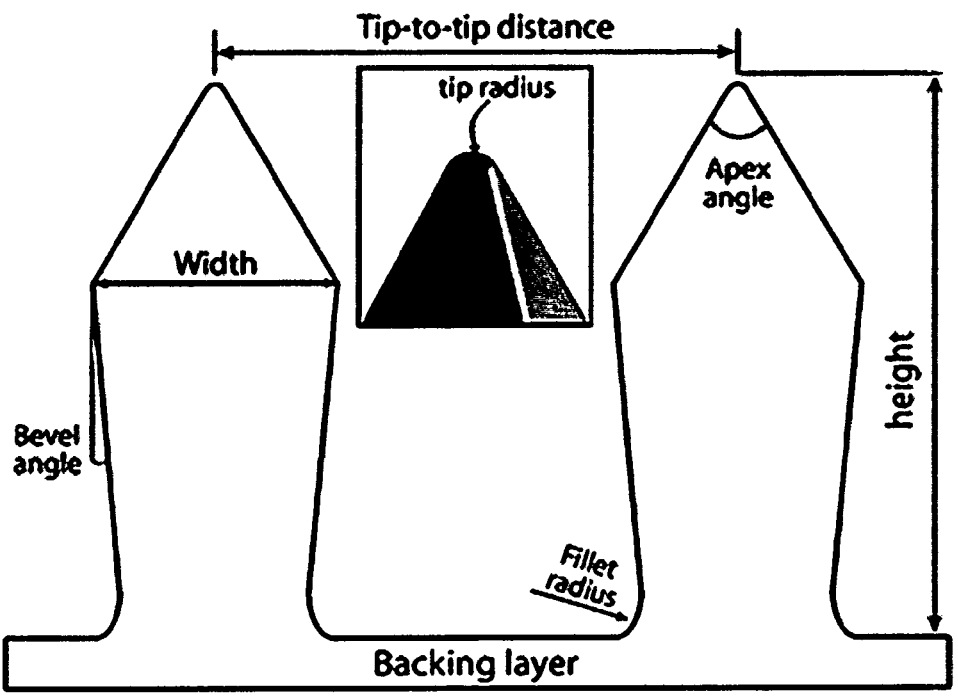
FIG. 6. LL-dMNAs geometric parameters.

The microfabrication process results in integration AAV-based sensor-drivers in the apex of the obelisk microneedles (see FIG. 6), or layered at different distances from the backing, enabling precise, efficient and cost effective drug delivery. Micromilling/spin-casting-based fabrication techniques are optimized to reproducibly create layer-loaded MNAs with clinically relevant MNA designs, including different geometric parameters, different dissolvable polymers, such as, without limitation carboxymethyl cellulose (CMC), trehalose, glucose, maltose, maltodextrin, silk-based polymers, and hyaluronic acid (HA), and combinations thereof, and different loading amounts (e.g., viral vector, drug, or carrier amounts). Briefly, microfabrication begins by fabricating precision master molds using diamond-tool micromilling, which is capable of creating complex geometries with micron-level precision on multitude of engineering materials. Micromilling permits precise needle and array geometries, and their spatial distribution. Subsequently, elastomer molding approach as described above is used to create Polydimethylsiloxane (PDMS) (or another elastomer of a flexible polymer) production molds. The third step of the technique, using spin casting to create final LL-dMNAs from the production molds is quite specific to particular biocargo materials: A solution of the dissolvable material and viral vector is first prepared in DI water. For layer-loading of AAV-based reporter genes, sufficient amount of the solution will be loaded into the elastomer mold and centrifuged at a specific temperature and speed until the dry bioactive cargo/dissolvable polymer mixture is located at the tip portion, or at a precise layer of the microneedles after tip-loading of the production mold with the dissolvable polymer mixture, optionally including a drug such as an antihistamine, an anti-inflammatory, and/or an immunosuppressant in the production molds. Next, the structural material that forms the rest of the needles and backing layer is fabricated from a dissolvable polymer by loading it in hydrogel form into the elastomer molds and centrifuging at a prescribed temperature and centrifugal speed until the full density, dry MNAs are obtained. The encapsulation efficiency and reproducibility of layer-loading of AAV-based reporter genes through the MNA fabrication process is evaluated through quantitative comparison of the target amount of AAV-based reporter genes to the amount that is actually encapsulated using real time polymerase chain reaction technique (qPCR) (after dissolving MNAs in PBS.) This is done for different dissolvable polymers, fabrication conditions, and loading amounts. Encapsulation efficiency is correlated with dissolvable polymer concentration used for layer-loading, the loaded amount of AAV-based sensor-drivers, and spin-casting conditions. Table 2 provides exemplary and non-limiting microneedle parameters.

TABLE 2

| A set of sample MNA parameters | |
|---|---|
| Height (μm) | 100, 200 |
| Width (μm) | 50, 100 |
| Apex angle (deg.) | 30, 45 |
| Bevel angle (deg.) | 0, 2, 5 |
| Fillet radius (μm) | 5, 15, 30 |
| Tip-to-tip (μm) | 350, 600 |

Separating-Tip LL-MNAs:

In certain instances, dissolution time required for high efficiency transduction could be long (e.g., 12-24 hrs), whereas the needle backing is preferably removed in shorter period of time (and thus the microneedle array does not have to stay on the skin for more than a few minutes). To address this, multi-material LL-dMNAs, where the viral-loaded layer, e.g. tip, is composed of a slow-dissolving (e.g., high molecular weight) polymer with the rAAV particles, and the needle stem, between the backing and loaded layer is made from a fast-dissolving material. As such, when applied, the needle base, between the backing and loaded layer, will dissolve away rapidly, e.g., within seconds or minutes, allowing separation of the viral-loaded portion of the microneedle, such as the loaded tips, from the backing, thereby ensuing slow dissolution for effective transduction. In use, the backing layer is removed after separation of the tips.

Large-Area LL-MNAs with Flexible Backing Layer:

Adequate spatial distribution of AAV reporters is desirable for more effective diagnosis strategies. This entails relatively larger MNAs designs. The described micromilling technique is used to create large-area master molds, which in turn enables fabrication of large-area LL-dMNAs with the favorable MNAs designs and processing conditions. In many instances, a flexible backing layer is preferred for the larger LL-dMNAs because conforming to the application area will be important for precision delivery (depth). The flexibility of the backing layer will allow the array of highly-dense micro-projections to conform the skin better to breach the stratum corneum more efficiently. As such, an elastomer, as are broadly-known is used in one aspect of the backing.

Because skin depth varies, a layer-loaded dissolvable MNA, with AAV reporters layered at designated levels (that is at layers of designated distances from the backing) is prepared. Micromilling, as described above, is used to create master molds with varying (non-uniform) needle heights between different sub-arrays. The spin-casting step is modified to encapsulate AAV reporters into different heights within a needle to control the targeted delivery depth of AAV-based sensor-drivers within skin microenvironments. Layered fabrication requires additional steps of loading and drying with precise amounts. The AAV-based reporters are embedded to desired height (that is, distance from the backing), which will then determine the delivery depth. Fabrication and needle design is described above.

Multi-array LL-dMNAs are prepared by selectively addressing individual needles with different AAV-based reporter genes. This may be used for large-area and variable-height layer-loaded dissolvable MNAs. In this example, inkjet deposition is used, for precise and reproducible tip-loading. After preparing the bioactive cargo solutions (for different AAV-based reporters), a custom inkjet-based material deposition system is used for selective deposition of different AAV reporters into individual needles for optimal spatial distribution (Campbell, P. G., et al., Tissue engineering with the aid of inkjet printers. *Expert Opin Biol Ther*, 2007. 7(8): p. 1123-7). This inkjet system integrates computer vision-based targeting calibration to achieve targeting accuracies of approximately 4 µm, and has been used for several diverse projects, relating to biological patterning using protein, quantum dot, and hormone 'bioinks' for tissue engineering and regenerative medicine applications (see, Cooper, G. M., et al., Inkjet-based biopatterning of bone morphogenetic protein-2 to spatially control calvarial bone formation. *Tissue Eng Part A*, 2010. 16(5): p. 1749-59 and Herberg, S., et al., Inkjet-based biopatterning of SDF-1beta augments BMP-2-induced repair of critical size calvarial bone defects in mice. *Bone*, 2014. 67: p. 95-103).

Example 3—Inflammation Panel

A panel of reporter genes are used to evaluate a patient's inflammation status. A panel of AAV reporters are therefore prepared that comprise TREs of one, two, three, or four or more of any combination of a NF-κB TRE, a CREB TRE, a STAT1 TRE, a STAT3 TRE, a STAT 1/2 heterodimer TRE, an IRF1 TRE, an NFAT TRE, a FOXO1 TRE, an ETS1 TRE, an AP-1 TRE, an HIF-1 TRE, an ETS-1 TRE, or a RELA TRE. Exemplary TRE sequences for these are provided above. The response to individual cytokines and stimulating agents are shown in Table 3.

TABLE 3

A set of sample transcription factors, model activators, and associated cytokines to be detected for the example application of inflammation detection/measurement

| Transcription Factor | Model Activator | Cytokine |
| --- | --- | --- |
| NFkB | LPS | TNFα |
| STAT1 | Ifn-γ | |
| STAT3 | IL-6 | |
| CREB | ATP | GM-CSF |
| STAT1/2 | Ifn-λ | |
| IRF1 | Ifn-x | Interferons |
| SRC-1 | Estrogen | Hormones |
| NFAT | $Ca^{2+}$ | TCR Prostaglandins |
| AP1 | LPS | TNFα, IL6, Ifn-γ |
| FOXO | LPS | TNFα (IL2 loss) |
| HIF1 | Hypoxia | IL1-β/TNFα |
| ETS-1 | IL1/TNFα | |

In one example, AAV vectors encoding reporter constructs are prepared for each of eight additional inflammation associated transcription factors, based on distinct, identified transcription factor binding sites (TREs) in the human genome, for example as shown above.

Example 4

Figure 7:
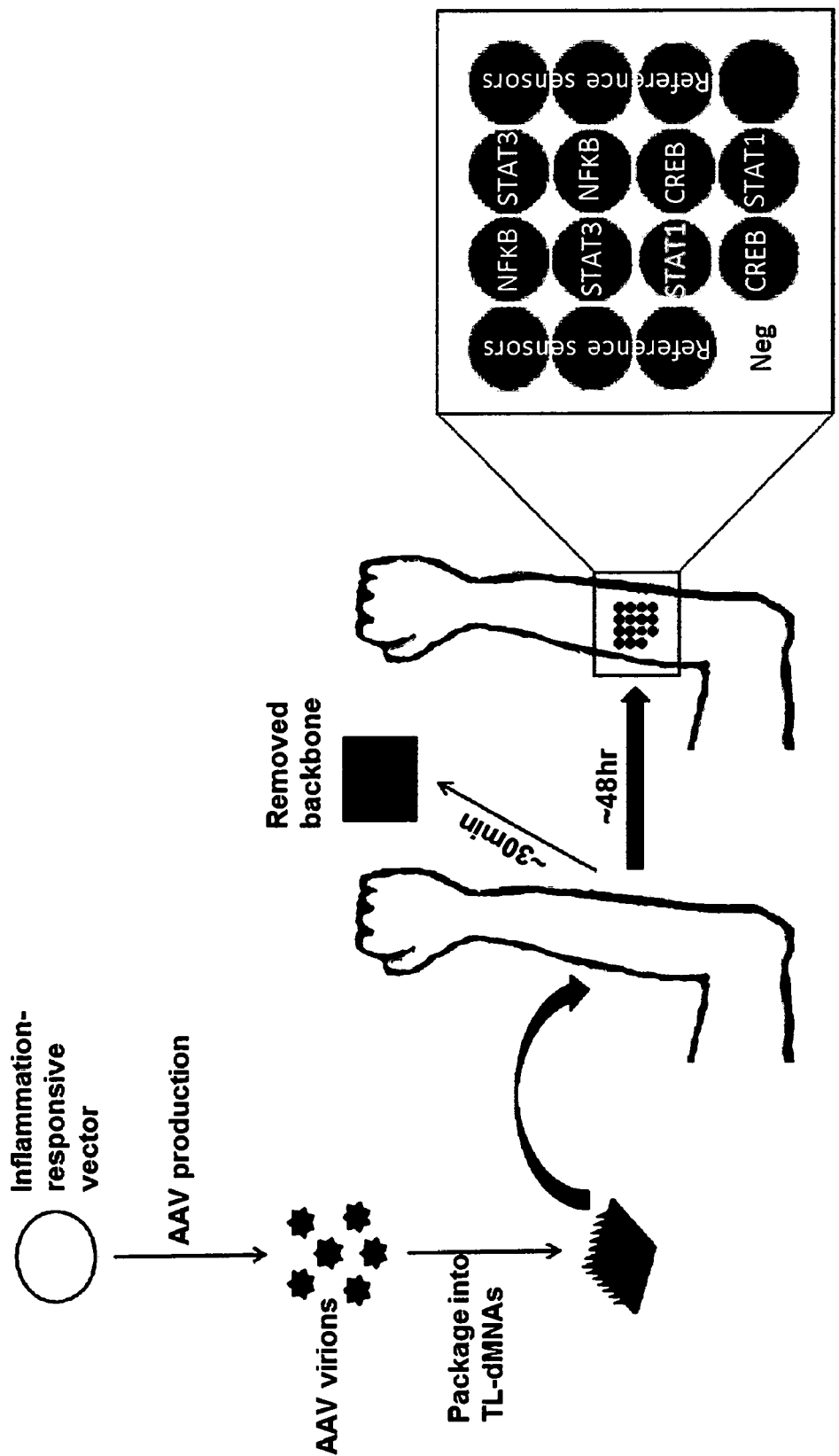
FIG. 7. Transformation of endogenous keratinocytes into real-time reporters of global inflammation, using LL-dMNA-delivered AAV vectors to deliver reporter DNA to the skin. An inflammation-responsive reporter plasmid is used to produce recombinant AAV (rAAV) particles, which are subsequently packaged into microneedle arrays that are applied to the skin. The needles quickly dissolve, allowing the rAAV particles to be released in 30 minutes or less. After ~48 hours, skin cells produce fluorescent protein in response to inflammatory transcription factor activity. This fluorescence can be measured through the skin using available in vivo imaging techniques (Kim S, et al. (2004) Near-infrared fluorescent type H quantum dots for sentinel lymph node mapping. *Nat Biotechnol* 22(1):93-97; Tanaka E, et al., (2006) Image-guided oncologic surgery using invisible light: completed pre-clinical development for sentinel lymph node mapping. *Ann Surg Oncol* 13(12):1671-1681; and Marshall M V, et al. (2012) Near-infrared fluorescence imaging in humans with indocyanine green: a review and update. 2(2):12-25). The response levels of inflammation reporters is normalized against constitutive reference genes that produce fluorescent protein at various fixed levels.

The following describes use of layer-loaded dissolvable microneedle arrays (LL-dMNAs) to deliver AAV through the stratum corneum. These arrays are composed of small needles, made with harmless biocompatible polymers, that pierce the skin and then dissolve, dispersing their cargo to the lower epidermis in an efficient and minimally invasive fashion. They cause nominal disruption of the skin and reproducibly deliver biocargo to the local skin environment. Therefore, LL-dMNAs will provide a highly controlled method for delivering inflammation-reporter AAV through the stratum corneum. LL-dMNAs will be used to deliver rAAV particles, packaged with inflammation-responsive reporter DNA, to keratinocytes of the lower epidermis (~1 mm delivery depth), which will then produce fluorescent proteins in response to global inflammation levels in the body (FIG. 7). The following describe the first steps in this process as proof of concept, namely, the search for an optimal AAV serotype for keratinocyte infection, the testing of TL-dMNAs' useability for in vivo AAV delivery, the construction and validation of a fluorescent reporter for the archetypal inflammatory transcription factor NF-κB, and the in-house production of AAV for eventual delivery of this reporter to cells.

Methods

In Vitro Cell Culture

HEK293 (ATCC #CRL-1573), AAVpro 293T (Clontech), and HaCaT (a broadly-available and well-known immortalized human keratinocyte cell line) cells were maintained in Dulbecco's Modified Eagle's Medium (DMEM) with 4.5 g/L glucose, L-glutamine, and sodium pyruvate (Mediatech) supplemented with 10% fetal bovine serum (FBS; Atlanta Biologicals) and 10 U/mL penicillin and streptomycin. All cells were grown in 37° C. incubators maintained at ~95% humidity and 5% $CO_2$. Cultures were monitored daily and passaged regularly at 80-90% confluence.

Fluorescence Microscopy

Fluorescence microscopy on cultured cells was performed using an Andor Revolution XD System with Spinning Disk (Andor Technology) with an oil immersion aprochromat 60× objective. Utilized laser lines were 488 nm (for eGFP, with 525/25 nm bandpass emission filter) and 560 nm (for TurboRFP, with 607/36 emission filter). Imaging data were collected using Andor iQ3 software (Andor Technology) and analyzed with ImageJ, an image analysis software package developed at the NIH. In vivo imaging of nude mouse model was achieved on an IVIS SpectrumCT imaging system (PerkinElmer). A 460 nm excitation filter was used to excite eGFP expression in the anaesthetized mouse flank, with 520 and 540 nm emission filters. Data were collected and analyzed via Living Image software (PerkinElmer).

Flow Cytometry

Flow cytometric analysis of cultured HEK293 and HaCaT cells was performed on two systems in the Carnegie Mellon University flow cytometry core. All cells were prepared for analysis via trypsinization, resuspension in fresh DMEM, and filtering through sterile Nytex membranes to avoid cell clumps. Commercial viral functional titer calculation and validation of in-house AAV production was performed on an Accuri C6 flow cytometer (BD Biosciences), using a 488 nm laser line and 533/30 filter to assay for eGFP expression. Data were collected and analyzed on ForeCyt software (Intellicyt). Testing and validation of TurboRFP-based inflammation-responsive constructs was performed on a FACS Vantage SE Flow Cytometer and FACS Diva option (BD Biosciences) using a 530 nm laser with 575/26 bandpass filter. Quantitation was performed using FACS Diva Software (BD Biosciences).

Commercial Viral Functional Titer Calculation

Control AAV vectors (AAV.CMV.PI.eGFP.WPRE.bGH) were obtained from the University of Pennsylvania Vector Core (Penn Vector Core) at known physical titers (viral particles [vp]/mL). To determine the functional titers (infectious units[IU]/mL) of these viruses, as well as to compare their ratios of infectious units to viral particles (IU/vp) in HEK293 and HaCaT cells, $5 \times 10^4$ cells were seeded to individual wells of a 12-well plate in complete DMEM (Mediatech). These cells were immediately transduced with control viruses at a known physical multiplicity of infection (MOI; vp/cell). 18-24 hr post-transduction, the cells were washed with PBS and the media replaced. At 44-48 hr, each set of transduced cells was resuspended and eGFP expression levels were analyzed on an Accuri C6 flow cytometer (BD Biosciences) as described above. Infected cells were gated by comparison with a negative control. The percentage of infected cells was determined for each transduction, and the Poisson law (fraction infected=$1-e^{MOI}$) used to calculate the functional MOI (IU/cell) of the control viruses as previously described(26). The ratio of IU/vp was calculated from the ratio of functional MOI to physical MOI obtained in this manner.

In Vivo Validation of MNA-Delivered AAVs

In vivo testing of TL-dMNAs loaded with AAV2-CMV-eGFP virus (PVC) was performed in the Mellon Institute Vivarium under the direction of Dr. Phil Campbell. A single nude mouse (Harlan Sprague Dawley Inc.) was temporarily anaesthetized via isoflurane inhalation and injected with TL-dMNAs containing AAV2-eGFP construct (~$4.5 \times 10^{10}$ viral particles) using a spring-loaded applicator. Injections were performed in the skin of the right ear, left flank, and right flank. Imaging of the nude mouse was performed at 24, 48, 72, and 144 hr post-injection on the IVIS SpectrumCT imaging system to assay for eGFP expression localized to the areas of injection.

Construction of NF-κB-Responsive AAV Vector

Figure 8:
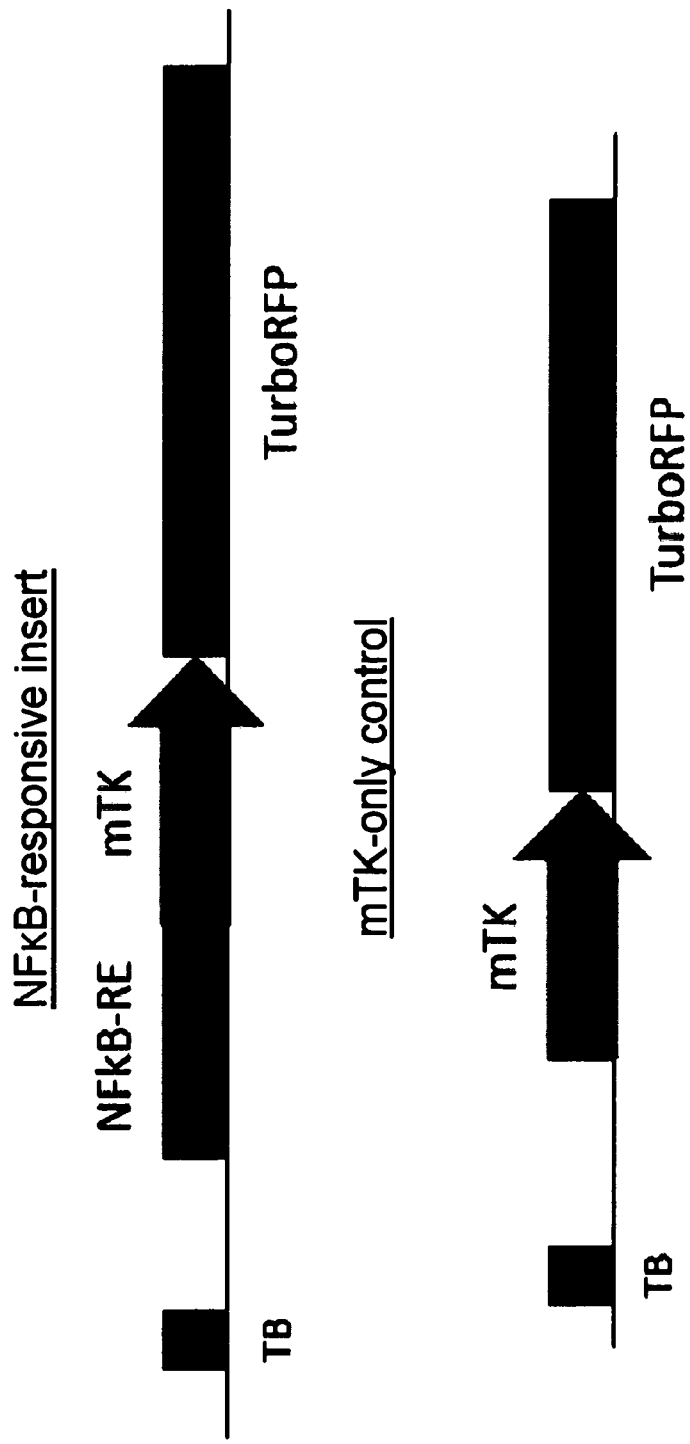
FIG. 8. NF-κB-responsive insert produces fluorescent reporter in response to transcription factor activation by TNFα. Inserts transfected into HEK293 cells (in pUC57 control plasmid from GenScript).

Promoterless AAV vector (pAAV-MCS; Cell Biolabs), containing an MCS and polyA site flanked by the inverted terminal repeats (ITRs) that define the AAV genome, was used as the plasmid backbone. An NF-κB-responsive sequence was assembled based on Clontech's pNF-κB-MetLuc2 plasmid and previously-published data on NF-κB-responsive AAV vector production (Chtarto A, et al. (2013) An adeno-associated virus-based intracellular sensor of pathological nuclear factor-B activation for disease-inducible gene transfer. *PLoS One* 8(1):e53156). Briefly, four repeats of the consensus NF-κB binding element were linked to TurboRFP (Evrogen) driven by a minimal thymidine kinase (mTK) promoter (FIG. 8). These elements were preceded by a transcriptional blocker site. In the final AAV genome, a polyA site will also be included; together, these elements will reduce constitutive promoter activity by the AAV ITR elements in the final construct. Bordering BamHI and BglII sites were inserted for simple transfer of the insert into the pAAV-MCS multiple cloning site. A non-responsive control construct, containing the mTK promoter but lacking the NF-κB response elements, was also designed. These sequences were sent to GenScript for synthesis and construct production. The resulting pUC57-NF-κB.RE plasmid, and pAAV-MCS, was doubly digested with BamHI and BglII and the products ligated to produce pAAV-NF-κB.RE-mTK-TurboRFP construct. The resulting NF-κB-responsive AAV genome was verified by both BamHI/BglII double digest (to confirm correct sizes of insert and backbone) and SmaI single digest (to confirm the integrity of the viral ITRs). All AAV vectors were transformed and grown in Stbl2 cells (F-mcrA Δ(mcrBC-hsdRMS-mrr) recA1 endA1 Ion gyrA96 thi supE44 relA1λ-Δ(lac-proAB); Invitrogen) in order to minimize recombination events between the viral ITRs.

Validation of Inflammation-Responsive Constructs

HEK293 and HaCaT cells were transfected with pUC57-NF-κB.RE-mTK-TurboRFP (inflammation-responsive) and pUC57-mTK-TurboRFP (control) constructs using Xfect transfection reagent (ClonTech). Three micrograms of DNA were used in all transfections, which were carried out according to manufacturer's protocol. Transfections were performed in cells grown without penicillin and streptomycin for at least 24 hours to avoid undesirable interactions between transfection complexes and anionic antibiotic compounds. Approximately 4 3 hr post-transfection, cells were treated with 100 ng/mL TNFα (gift of Ceren Tuzmen, Carnegie Mellon University) and allowed to incubate for 5 hr. Cells were then lifted and analyzed on the FACS Vantage SE flow cytometer to assay for TurboRFP expression as described above. Mean fluorescence intensity was determined in order to quantify any change upon NF-κB stimulation.

Adeno-Associated Virus Production

AAV was produced using the AAVpro Helper Free System (Clontech) and a cis-plasmid from the University of Pennsylvania Vector Core. Briefly. AAVpro 293T cells were triply-transfected with pHelper, rep2/cap2, and pAAV.CMV.PL.eGFP.WPRE.bGH (Penn Vector Core) constructs via CalPhos mammalian transfection reagent (Clontech) according to manufacturer's protocol. Cells were grown overnight before being placed in DMEM with 2% FBS. Two days later (72 hr post-transfection), viruses were harvested from the cells using proprietary AAV extraction solutions from Clontech. All isolated viruses were stored at −80° C. Approximate functional titers (infectious units/mL) were obtained by performing transductions in HEK293 cells ($5\times10^4$) in a 12-well plate using threefold serial dilutions of virus. Media was changed at 24 hr post-transduction and cells were analyzed on the Accuri C6 flow cytometer at 48 hr. The percentage of infected cells was determined from comparison with a negative control, and the functional titer calculated from this number using the Poisson law as described above. Physical titer (vp/mL) was obtained using the ratio of IU/vp calculated for AAV2-CMV-eGFP during initial tests of control virus from the University of Pennsylvania Vector Core.

Screening of AAV Serotypes for Optimal Keratinocyte Infection

A large number of AAV serotypes have been developed for different purposes in the lab (Samulski R J, et al. (2014) AAV-Mediated Gene Therapy for Research and Therapeutic Purposes. *Annu Rev Virol* 1(1):427-451). The proteins that form the viral capsid vary between serotypes, leading to different patterns of cell-surface receptor binding. Because of this, separate AAV serotypes can have widely different infectivity patterns or tropisms for various cell types in vitro and in vivo. AAV research to date has tended to focus on transduction of a small number of model tissues, including liver, muscle, brain, and eye. For the purposes of this project, it will be necessary to use a serotype of AAV with a high level of infectivity for skin cells. High infectivity in keratinocytes will minimize the amount of virus required for later assays and will ensure that viral doses deliverable by TL-dMNAs will infect enough cells to allow visibility of inflammation-responsive fluorescence through the skin. Ideally, the chosen AAV vector should be highly selective for keratinocytes to reduce the risk of off-target cell infection in the skin microenvironment.

Figure 9A:
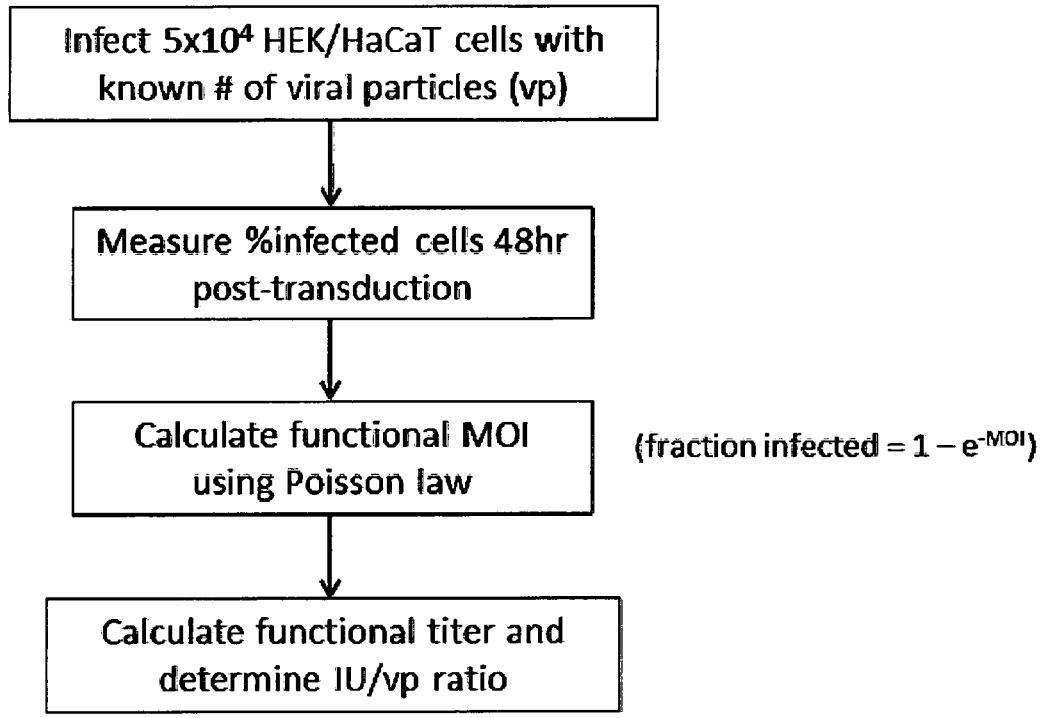
(FIG. 9A) Workflow of transduction efficiency comparison experiments. Functional MOI=infectious units/cell, which was compared with the known physical MOI (viral particles/cell) to determine the ratio of infectious units/viral particles.

In order to compare the infectivity of multiple AAV serotypes in keratinocytes, control viruses were obtained from the University of Pennsylvania Vector Core. These viruses encode the gene for eGFP, a popular and widely-used fluorescent protein, linked to the strong, constitutively-active CMV promoter. CMV-eGFP provides a simple, high-expression system with few variables, allowing simple comparisons between AAV serotypes' transduction efficiencies. These control viruses were used to transduce HEK293 cells as a baseline against which further transduction studies could be compared. Additionally, HaCaT cells—an established in vitro analogue of human keratinocytes—were employed as a model system closer in behavior to in vivo skin cells. The workflow for the transduction efficiency comparison experiments is shown in FIG. 9A. Briefly, 50,000 HEK293 or HaCaT cells were transduced with a known number of viral particles. Two days later (a standard timepoint for in vitro AAV transduction analysis), flow cytometry analysis of the percentage of infected cells was used to determine the ratio of functional infectious units to total viral particles for each serotype in both cell types.

Figure 9B:
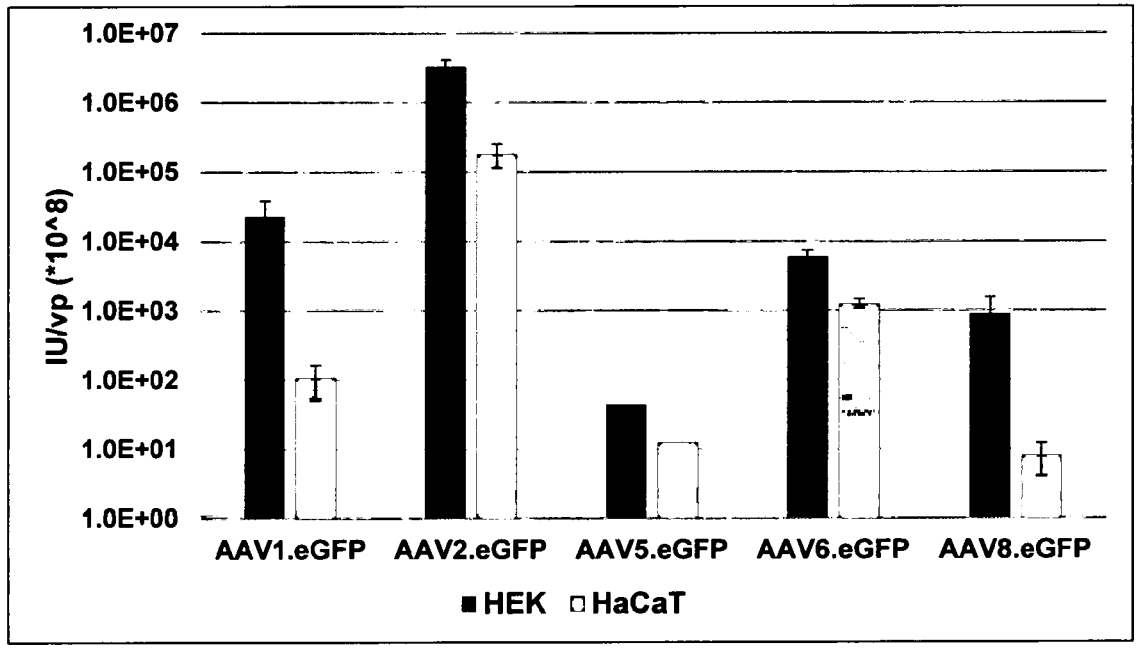
(FIG. 9B) Transduction efficiency comparison results, in logarithmic scale. Data shown is the ratio of infectious units to total viral particles (IU/vp) for both HEK293 and HaCaT cells (data is multiplied by $10^8$ for visual clarity). The IU/vp ratio is directly proportional to viral infectivity in a particular cell type. AAV5.eGFP results lack error bars due to currently unfinished set of experiments. These experiments will be performed again in fresh HaCaTs due to the possibility of *mycoplasma* contamination in the cell stocks used to generate these data.

The results of these transduction experiments are shown in FIG. 9B. AAV of serotype 2 (AAV2) exhibits the highest infectivity in both HEK293 and HaCaT cells of any of the viral serotypes (1, 2, 5, 6, and 8) currently tested. AAV6 exhibits comparatively moderate transduction efficiency in HaCaTs, with other strains much less infective. All tested strains are more infectious in HEK293 cells than in HaCaTs. These data are at odds with currently reported data in the literature. A recent survey of AAV serotype transduction efficiencies in various human tissues found AAV2 to have a very low infectivity in cultured primary human keratinocytes, with AAVs 1 and 6 exhibiting significantly higher in vitro efficiencies (Ellis B L, et al. (2013) A survey of ex vivo/in vitro transduction efficiency of mammalian primary cells and cell lines with Nine natural adeno-associated virus (AAV1-9) and one engineered adeno-associated virus serotype. *Virol J* 10(1):74). The conflict is unlikely to be an issue of experimental design differences, as the transduction efficiencies reported here for HEK293 cells are in line with those reported by Ellis et al. This suggests that HaCaTs may not be an adequate model of human keratinocyte AAV transduction efficiency.

Future infectivity comparison experiments will attack these discrepancies from two directions. First, these AAV serotypes will be used to infect human skin explants ex vivo, and the fluorescence intensity of skin sections will be measured to provide a more accurate model of the transduction efficiency of AAV toward in vivo skin cells. Second, HaCaTs will be grown in low-calcium growth medium to induce a less differentiated phenotype (Boukamp P (1988) Normal Keratinization in a Spontaneously Immortalized. 106(March):761-771 and Deyrieux A F, et al. (2007) In vitro culture conditions to study keratinocyte differentiation using the HaCaT cell line. *Cytotechnology* 54(2):77-83), more akin to the lower epidermal keratinocytes that will be transduced by microneedle arrays, and further transduction efficiency experiments will be compared to the present results.

Figure 10:
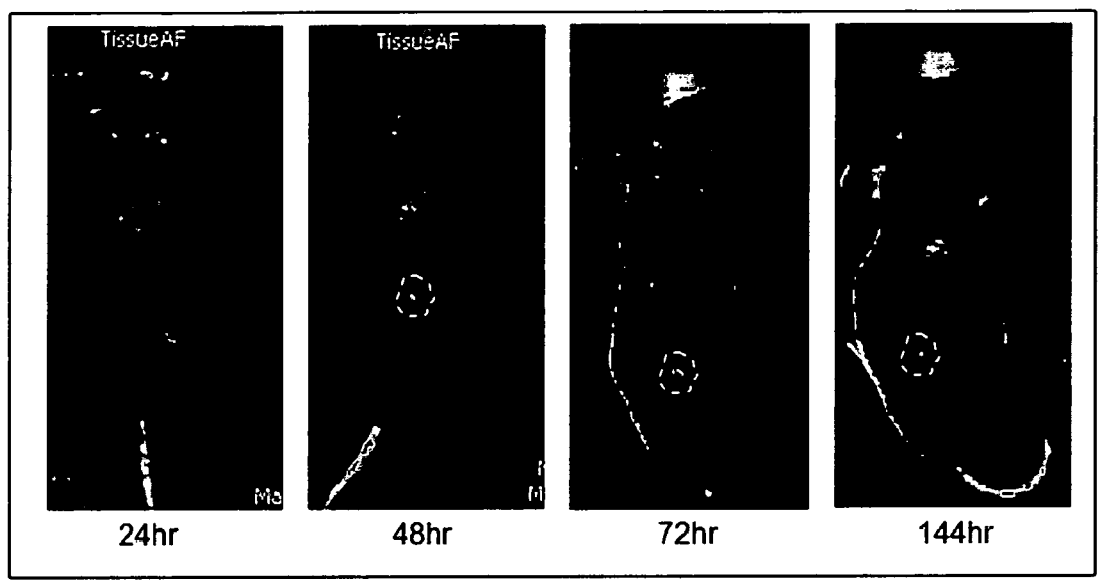
FIG. 10. Deposition of AAV2-CMV-eGFP into nude mouse skin via LL-dMNA deposition produces a highly localized fluorescence pattern. Nude mouse was imaged using a tungsten halogen lamp passed through a 460 nm excitation filter to excite eGFP; emitted fluorescence was collected using a 520 nm filter. eGFP expression at one of three LL-dMNA deposition sites was detected at 48 hours post-injection and at later timepoints; this site is highlighted by a dashed circle. Background fluorescence, particularly high in the tail, is most likely the result of tissue autofluorescence.

In Vivo Validation of AAV Delivery Via Tip-Loaded Dissolvable Microneedle Arrays An optimal AAV serotype for keratinocyte infection in this project has yet to be identified, but AAV2 has proven itself capable of infecting a wide array of cell types. For this reason, control AAV2 virus was used to test the useability of TL-dMNAs for in vivo AAV delivery into the skin microenvironment and to ensure that AAV transduction efficiency was not destroyed during packaging into microneedle arrays. AAV2-CMV-eGFP was packaged into microneedle arrays using a two-step spin-casting technique as described herein. Shortly after fabrication, these arrays were pressed into the skin of a nude mouse model in three locations: left flank, right flank, and right ear. Subsequent imaging revealed that one of these injections sites (right flank) exhibited pronounced localized fluorescence in the 520-540 nm range at 48 hr post-injection onward (FIG. 10). Failure of the other two injection sites to evoke eGFP expression is most likely attributable to TL-dMNA application failure, as deployment in mouse skin proved difficult to perform without damaging the surrounding tissue. These issues can be solved using a spring-loaded applicator to apply uniform pressure in TL-dMNA applications (Korkmaz E, et al. (2015) Therapeutic intradermal delivery of tumor necrosis factor-alpha antibodies using tip-loaded dissolvable microneedle arrays. *Acta Biomater* 24:96-105).

These results are distinctly encouraging for two reasons: first, they show that AAV vectors survive the TL-dMNA packaging process with high enough viability to evoke visible fluorescent reporter production through the skin; second, the highly localized pattern of transduction suggests that AAVs delivered via microneedle array will stay contained at the injection site as desired, rather than spreading out in the skin microenvironment and causing more diffuse fluorescence.

Production of an NF-κB-Responsive Fluorescent Reporter AAV Genome

Among the most biologically significant and widely studied of the inflammatory transcription factors is nuclear factor κB (NF-κB). NF-κB is a dimeric transcription factor activated by a wide variety of pro-inflammatory stimuli, including various cytokines, pathogenic infections, and UV radiation. Signaling pathways activated by NF-κB interact with numerous other inflammatory transcription factors and influence nearly every aspect of cellular homeostasis. Due to the familiarity of this transcription factor and wide body of literature associated with it, NF-κB will serve as an ideal platform for demonstrating delivery of inflammation-responsive AAV vectors using TL-dMNAs.

Figure 11A:
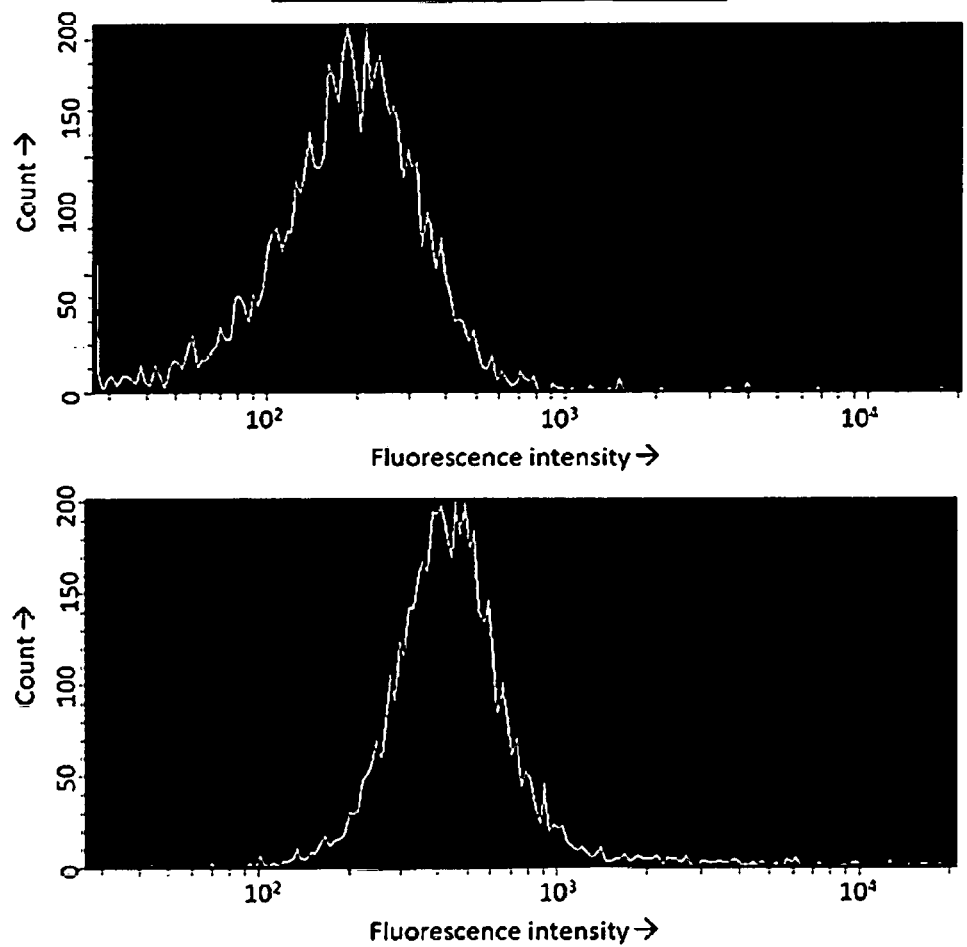
(FIG. 11A) Fluorescence histograms collected on FACS Vantage SE. (Top) Transfected HEKs not treated with TNFα show no fluorescence enhancement. (Bottom) HEKs treated with 100 ng/mL TNF-α for 5 hours show increased fluorescence intensity.
Figure 11B:
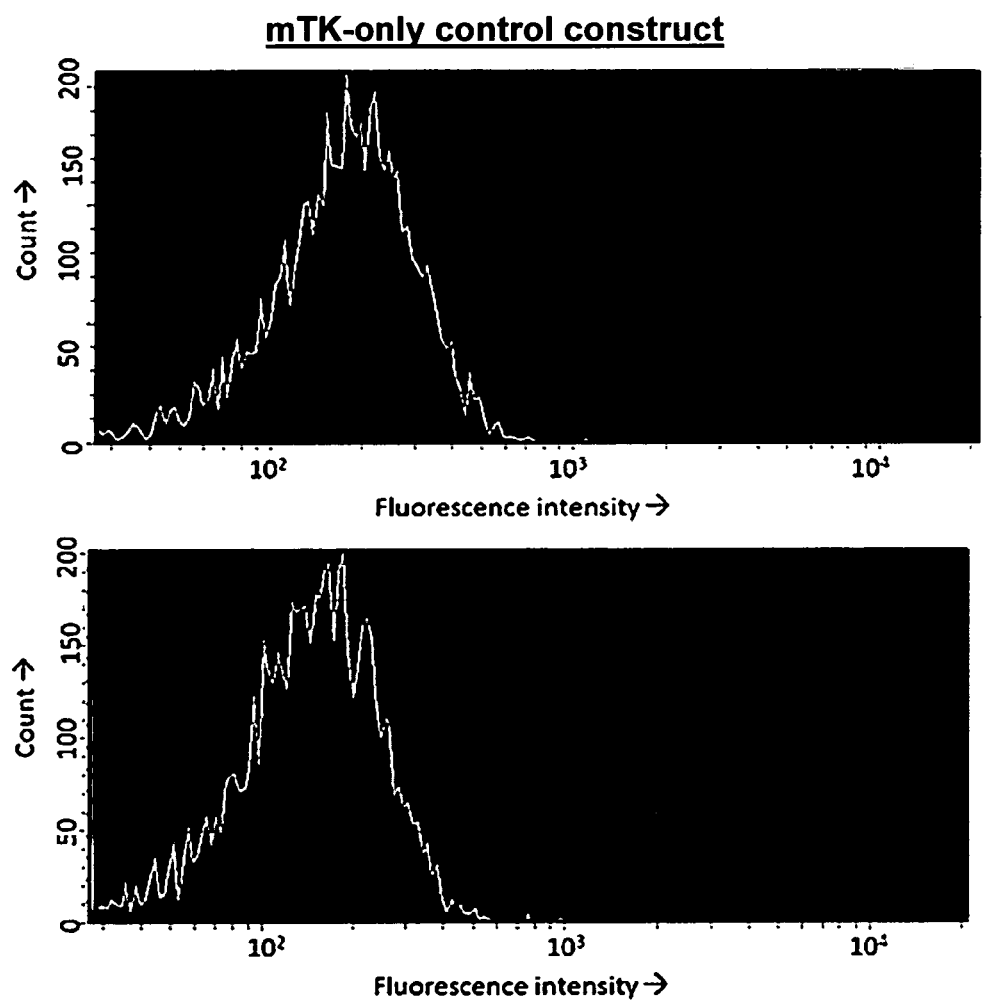
(FIG. 11B) HEKs transfected with mTK-only control construct (lacking an NF-κB binding site) show no fluorescence enhancement without (Top) or with (Bottom) TNF-α treatment. TurboRFP fluorescence was excited using a 536 nm laser and collected with a 575/26 bandpass emission filter. "Count" (y-axis)=count of recorded events fluorescing at given intensity. Fluorescence intensity (x-axis) is in arbitrary units.

An NF-κB-responsive insert was constructed similar to that of Chtarto A, et al., An adeno-associated virus-based intracellular sensor of pathological nuclear factor-κB activation for disease-inducible gene transfer. *PLoS One* (2013) 8(1):e53156. The insert utilized an NF-κB consensus binding site from a commercially available plasmid. This was linked to TurboRFP to produce fluorescent reporter in response to NF-κB stimulation (FIG. 8). This insert, and a control lacking the NF-κB binding site, was synthesized by GenScript. The resulting plasmid (pUC57-NF-κB.RE-mTK-TurboRFP) was used to transfect HEK293 cells to verify the responsiveness of the insert to NF-κB stimulation. Transfected cells were treated with TNFα, a canonical activator of NF-κB and TurboRFP expression was measured via fluorescence microscopy and flow cytometry. Cytometry results are shown in FIG. 11A. NF-κB stimulation led to a clear increase in TurboRFP expression. This result was not seen in cells transfected with a control construct lacking the NF-κB response element (FIG. 11B). The relatively mild rise in ~575 nm fluorescence (~2-4-fold, with a plateau reaching up to ~100-fold) can be increased during further optimization of the inflammation-responsive insert: namely, changing the minimal promoter to a more active one (e.g. minimal CMV, or mCMV) and increasing the number of NF-κB response element repeats.

Similar transfection experiments were performed in HaCaT cells, but no increase in TurboRFP expression on NF-κB stimulation was observed. Follow-up tests found these HaCaTs to have remarkably low transfection efficiency using both Xfect and Lipofectamine 3000 (Invitrogen) reagents. This might have been a side effect of *mycoplasma* contamination, but HaCaTs are generally known to have low capacity for transfection. To remove these factors, fresh HaCaTs will be infected with virus carrying this NF-κB-responsive reporter to validate its activity in keratinocyte analogues.

In the meantime, this insert has been adapted into an AAV genome for production of prototype inflammation sensor viruses. The NF-κB-responsive element was inserted into an AAV vector plasmid, and the integrity of the construct was verified by diagnostic restriction digests. This construct (pAAV-NF-κB.RE-mTK-TurboRFP) will be used to produce AAV2 transduction particles for subsequent testing. Once purified, the particles will be packaged into TL-dMNAs to transform cells in vitro and er vivo into NF-κB reporters, providing further proof-of-concept for the first steps shown in FIG. 7.

Production of Control AAV

As work on the NF-κB-responsive AAV genome continues, control AAV has also been produced to validate currently-available virus production schemes and determine the concentration of virus particles obtainable using these methods. In order to simplify initial production, a control AAV genome plasmid (pAAV-CMV-eGFP) was obtained from Penn Vector Core. This plasmid was combined with Clontech's AAVpro Helper Free System to generate AAV2-CMV-eGFP virus. Produced virus was used to transduce 50,000 HEK293 cells in a 1:3 serial dilution, and the number of infected cells was calculated 48 hours post-infection to determine the concentration of viral particles present and approximate the viral yields obtainable using this production scheme.

Fifty thousand HEK cells were treated with 33 uL of either DMEM media (negative control) or (B) a 1:3 dilution of produced virus. Percentage of infected cells was determined via cytometry. Data was plotted as FL1-A detector signal (533/30 nm emission filter) vs. FL2-A signal (585/40 nm). eGFP expression was detectable in both of these channels. Infected cells were gated compared to the negative control, and ForeCyt software was used to determine the approximate percentage of infected cells relative to the entire Population 2 (total HEK293 cells).

For Table 4, 33 μL of AAV2-CMV-eGFP virus (undiluted and through five 1:3 serial dilutions) was added to 50,000 HEK293 cells. 48 hours post-infection, the percentage of eGFP-expressing cells was measured on an Accuri C6 flow. These data were used to calculate the functional and physical titers of the produced virus. Only the lowest four data points (1:9-243 dilutions) were used to estimate the viral titer, as titer approximations obtained from high (>approx. 40%) percentages of infected cells tend to underestimate the actual value (Grigorov B, et al. (2011) Rapid titration of measles and other viruses: optimization with determination of replication cycle length. *PLoS One* 6(9):e24135).

TABLE 4

| Virus dilution: | Undiluted | 1:3 | 1:9 | 1:27 | 1:81 | 1:243 |
| --- | --- | --- | --- | --- | --- | --- |
| % infected: | 88.8 | 74.9 | 39.8 | 12.2 | 7.8 | 2.6 |

High viral titers (~$10^{12}$-$10^{13}$ vp/mL) will be required for later in vivo experiments, where larger numbers of viral particles must be administered to ensure a response (Keswani S G, et al. (2012) Pseudotyped adeno-associated viral vector tropism and transduction efficiencies in murine wound healing. *Wound Repair Regen* 20(4):592-600). As indicated above, protocols are available in the literature for concentration and purification of AAV vectors, allowing production of virus at these high concentrations.

DISCUSSION

The goal of this project is to overcome these limitations by developing a method for real-time monitoring of global inflammation levels in vivo, using microneedle array-delivered AAVs to carry inflammation-responsive fluorescent reporters to endogenous skin cells. These sensors will provide direct feedback on inflammatory transcription factor activity, allowing rapid assessment and control of clinical therapeutics and other anti-inflammatory technologies. The long-term potential to increase our understanding of inflammatory genetic networks and improve human health is high.

Results have provided several important confirmations for the techniques that will be used in this project. Deployment of AAV to a living mouse via microneedle array showed that this method of subcutaneous virus delivery is possible and results in a highly localized patch of fluorescence. In the long run, this will simplify the visual resolution of co-delivered inflammation-responsive reporters through the skin, an important factor in the success of this method. The development of an inflammation-responsive AAV genome provides both a template for future inflammation sensor constructs and a proof-of-concept for AAV-packaged, TL-dMNA-delivered inflammation sensors in general The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

The following clauses are illustrative of various aspects of the present invention.

1. A microneedle array comprising:
   a. a backing; and
   b. a plurality of microneedles attached to a side of the backing and comprising a first nucleic acid comprising a first gene encoding a colorimetric protein under transcriptional control of a vertebrate transcription factor-responsive element (TRE) such that when transfected into a vertebrate cell, the gene is expressed differently in the presence of a vertebrate transcription factor that binds the TRE than in the absence of the transcription factor and the difference in expression of the gene is optically detectable.

2. The microneedle array of clause 1, wherein the microneedles further comprises one or more additional, different nucleic acids, with each of the one or more additional, different nucleic acids comprising a gene encoding a colorimetric protein that is the same or different from the colorimetric protein of the first gene, responsive to the same or different transcriptional control than the first gene.

3. The microneedle array of clause 2, wherein a single microneedle comprises two or more of the different nucleic acids that produce different, separately addressable colorimetric proteins, such as two different fluorescent proteins that have distinguishable excitation and/or emission spectra.

4. The microneedle array of clause 2, in which microneedles containing the nucleic acids of the first gene and the second gene are located in discrete, addressable locations within individual or clusters of microneedles, such that when deposited in the skin of a patient, a colorimetric response is spatially patterned.

5. The microneedle array of any of clauses 1-4, wherein at least a portion of the microneedles comprising the nucleic acids, are dissolvable or bioerodible in vivo.

6. The microneedle array of any of clauses 1-5, wherein the nucleic acid is packaged in a viral transducing particle.

7. The microneedle array of clause 6, in which the viral transducing particle is an adenovirus, a herpes simplex virus, a gammaretrovirus, or a lentivirus transducing particle.

8. The microneedle array of clause 6, wherein the viral transducing particle is an Adeno-associated virus (AAV) transducing particle.

9. The microneedle array of clause 8, wherein the nucleic acid is a self-complementary AAV genome.

10. The microneedle array of any of clauses 1-9, wherein the colorimetric protein is a fluorescent protein.

11. The microneedle array of clause 10, wherein which the fluorescent protein is a green, yellow, cyan, red, far-red or near-infrared fluorescent protein, and optionally a far-red or near-infrared fluorescent protein.

12. The microneedle array of clause 11, wherein the fluorescent protein is a far-red or near-infrared fluorescent protein, and the far-red or near-infrared fluorescent protein is one of eqFP578, Katushka, mKate, mNeptune, e2-Crimson, TagRFP657, mCardinal, iRFP670, iRFP682, iRFP702, iRFP(iRFP713), iRFP720, iSplit, PAiRFP1, PAiRFP2, mCherry, tdTomato, DsRed-Monomer, dsRed-Express2, dsRed-Express, dsRed2, asRed2, mStrawberry, mRuby, mApple, jRed, HcRed1, mRaspberry, dKeima-Tandem, mPlum, AQ143, mIFP, iFP1.4, iFP2.0, or NirFP.

13. The microneedle array of any of clauses 1-12, in which the first gene is under transcriptional control of a transcription control sequence comprising a transcriptional response element (TRE), optionally including a minimal cytomegalovirus (CMV) promoter 3' to the TRE.

14. The microneedle array of any of clauses 1-13, wherein the first gene is under transcriptional control of a TRE chosen from: AP-1 TRE, C/EBPalpha TRE, c-Fos TRE, c-Jun TRE, c-Myc TRE, c-Rel TRE, DP-1 TRE, E2F+p107 TRE, E2F-1 TRE, E2F-4/DP-2 TRE, Egr-1 TRE, ErbA TRE, FosB TRE, HIF-1 TRE, HSF1 TRE, INF TRE, JunD TRE, Max1 TRE, NF-κB TRE, N-Myc TRE, p53 TRE, REVERB-alpha TRE, Sp1 TRE, Sp3 TRE, SRF TRE, YY1 TRE, NFAT TRE, FOXO1 TRE, ETS-1 TRE, RELA TRE, STAT1 TRE, STAT2 TRE, STAT1/2 TRE, STAT3 TRE, CREB TRE, IRF1 TRE, and/or SRC-1 TRE, and optionally chosen from NF-κB TRE, a CREB TRE, a STAT1 TRE, a STAT3 TRE, a STAT 1/2 heterodimer TRE, an IRF1 TRE, an NFAT TRE, a FOXO1 TRE, an ETS1 TRE, an AP-1 TRE, an HIF-1 TRE, an ETS-1 TRE, or a RELA TRE, and optionally wherein the microarray contains at least 1 or more, 2 or more, 3 or more, 4 or more, 5 or more, 6 or more, 7 or more, 8 or more, 9 or more, or 10 or more additional discrete, addressable locations, independently, a nucleic acid comprising a second reporter gene encoding a colorimetric protein under transcriptional control of a TRE different from that of the first gene, the RE chosen from one or more of AP-1 TRE, C/EBPalpha TRE, c-Fos TRE, c-Jun TRE, c-Myc TRE, c-Rel TRE, DP-1 TRE, E2F+p107 TRE, E2F-1 TRE, E2F-4/DP-2 TRE, Egr-1 TRE, ErbA TRE, FosB TRE, HIF-1 TRE, HSF1 TRE, INF TRE, JunD TRE, Max1 TRE, NF-κB TRE, N-Myc TRE, p53 TRE, REVERB-alpha TRE, Sp1 TRE, Sp3 TRE, SRF TRE, YY1 TRE, NFAT TRE, FOXO1 TRE, ETS-1 TRE, RELA TRE, STAT1 TRE, STAT2 TRE, STAT1/2 TRE, STAT3 TRE, CREB TRE, IRF1 TRE, and/or SRC-1 TRE, and optionally from NF-κB TRE, a CREB TRE, a STAT1 TRE, a STAT3 TRE, a STAT 1/2 heterodimer TRE, an IRF1 TRE, an NFAT TRE, a FOXO1 TRE, an ETS1 TRE, an AP-1 TRE, an HIF-1 TRE, an ETS-1 TRE, or a RELA TRE.

15. The microneedle array of any of clauses 1-14, wherein the first gene is under transcriptional control of a TRE chosen from: one or more iterations of an NF-κB TRE, a CREB TRE, a STAT1 TRE, a STAT3 TRE, a STAT 1/2 heterodimer TRE, an IRF1 TRE, an NFAT TRE, a FOXO1 TRE, an ETS1 TRE, an AP-1 TRE, an HIF-1 TRE, an ETS-1 TRE, or a RELA TRE.

16. The microneedle array of any of clauses 1-14, further comprising a microneedle or cluster of microneedles at a discrete, addressable location on the microneedle array one or more reference reporter genes, each independently comprising a nucleic acid comprising a gene under transcriptional control of a constitutive promoter, housekeeping promotor such as actin, tubulin, GAPDH, vinculin, cyclophilin B, cofilin, Lamin B1, HSP60, CoxIV, PCNA, or an inducible promotor such as a tet-inducible promotor, and encoding a colorimetric protein.

17. The microneedle array of any of clauses 1-16, wherein the nucleic acids are placed in layers in the microneedles at a distance from the backing of at least 50 μm, from 50 μm to 750 μm, or from 50 μm to 500 μm.

18. The microneedle array of any of clauses 1-16, wherein the nucleic acids are placed in layers in the microneedles, and wherein the microneedles comprise one or more additional nucleic acids, nucleic acids comprising reporter genes, optionally constitutive or control reporter genes, drugs, or excipients placed in one or more additional layers.

19. A method of monitoring an analyte in a patient comprising injecting at least the first nucleic acid at a site in the skin of a patient with the microneedle array of any of clauses 1-18 to produce a biosensor tattoo; and detecting expression of at least the first gene by detecting, if present, a color intensity change at one or more addressable locations in the biosensor tattoo due to expression of the colorimetric protein of at least the first gene.

20. The method of clause 19, wherein the color change is detected by imaging or scanning the biosensor tattoo and analyzing the image or scan by a computer method to detect any difference in color intensity of the skin at one or more wavelengths, at one or more addressable locations in the biosensor tattoo.

21. The method of one of clauses 19-20, wherein the colorimetric protein is a fluorescent protein, and expression of the genes is detected by illuminating the biosensor tattoo with light at an excitation wavelength of the colorimetric protein, and expression of the genes is detected by determining fluorescent intensity of the colorimetric protein at an emission wavelength of the colorimetric protein.

22. The method of any one of clauses 19-21, wherein the presence of an analyte as detected by expression levels of at least the first gene, as determined by imaging or scanning the biosensor tattoo, is related in a computer-implemented method to the presence of a disease or condition in a patient.

23. The method of clause 22, wherein the disease or condition associated with the analyte is: diabetes; obesity; inflammation, autoimmune disease and conditions; pulmonary and heart disease; infection; sepsis; presence of a biochemical warfare agent; presence of toxins; presence of or amount of one or more drugs; allergies; systemic levels of cortisol; presence of specific ions; presence of specific nutrients; presence of specific neurotransmitters; or presence of specific mental illness treatment drugs.

24. The method of clause 20, wherein the illumination and detection of the biosensor tattoo is performed by a device comprising:
  a. emitters, such as light-emitting diodes (LEDs) or organic light-emitting diodes (OLEDs) that produce light at an excitation wavelength of the colorimetric proteins;
  b. an imaging sensor, such as a CCD or CMOS sensor;
  c. a processor;
  d. data storage;
  e. computer-implemented instructions implemented by the processor for storing image data obtained from the imaging sensor in the data storage, and optionally one or more of analyzing the data to produce an output relating to expression levels of at least the first gene, transmitting data to and from the device, and/or outputting the image data and/or information produced by analysis of the image data;
  f. optionally, a wireless or wired communication module for transmitting data from the device to and optionally from a computer; and
  g. optionally, a display for providing output produced by the computer-implemented instructions.

25. The method of clause 24, in which the device is a smart-device, such as a smartphone, a smartwatch, or a wearable device, such as a band or a strap.

26. The method of any of clauses 19-25, for monitoring inflammation in a patient, wherein the first gene is under transcriptional control of a TRE chosen from: AP-1 TRE, C/EBPalpha TRE, c-Fos TRE, c-Jun TRE, c-Myc TRE, c-Rel TRE, DP-1 TRE, E2F+p107 TRE, E2F-1 TRE, E2F-4/DP-2 TRE, Egr-1 TRE, ErbA TRE, FosB TRE, HIF-1 TRE, HSF1 TRE, INF TRE, JunD TRE, Max1 TRE, NF-κB TRE, N-Myc TRE, p53 TRE, REVERB-alpha TRE, Sp1 TRE, Sp3 TRE, SRF TRE, YY1 TRE, NFAT TRE, FOXO1 TRE, ETS-1 TRE, RELA TRE, STAT1 TRE, STAT2 TRE, STAT1/2 TRE, STAT3 TRE, CREB TRE, IRF1 TRE, and/or SRC-1 TRE, and optionally chosen from NF-κB TRE, a CREB TRE, a STAT1 TRE, a STAT3 TRE, a STAT 1/2 heterodimer TRE, an IRF1 TRE, an NFAT TRE, a FOXO1 TRE, an ETS1 TRE, an AP-1 TRE, an HIF-1 TRE, an ETS-1 TRE, or a RELA TRE, and wherein the microarray contains at 1 or more, 2 or more, 3 or more, 4 or more, 5 or more, 6 or more, 7 or more, 8 or more, 9 or more, or 10 or more additional discrete locations, independently, a nucleic acid comprising a reporter gene encoding a colorimetric protein under transcriptional control of a TRE different from that of the first gene, the TRE chosen from one or more of AP-1 TRE, C/EBPalpha TRE, c-Fos TRE, c-Jun TRE, c-Myc TRE, c-Rel TRE, DP-1 TRE, E2F+p107 TRE, E2F-1 TRE, E2F-4/DP-2 TRE, Egr-1 TRE, ErbA TRE, FosB TRE, HIF-1 TRE, HSF1 TRE, INF TRE, JunD TRE, Max1 TRE, NF-κB TRE, N-Myc TRE, p53 TRE, REVERB-alpha TRE, Sp1 TRE, Sp3 TRE, SRF TRE, YY1 TRE, NFAT TRE, FOXO1 TRE, ETS-1 TRE, RELA TRE, STAT1 TRE, STAT2 TRE, STAT1/2 TRE, STAT3 TRE, CREB TRE, IRF1 TRE, and/or SRC-1 TRE, and optionally from NF-κB TRE, a CREB TRE, a STAT1 TRE, a STAT3 TRE, a STAT 1/2 heterodimer TRE, an IRF1 TRE, an NFAT TRE, a FOXO1 TRE, an ETS1 TRE, an AP-1 TRE, an HIF-1 TRE, an ETS-1 TRE, or a RELA TRE.

27. The method of any of clauses 19-26, for monitoring inflammation in a patient, wherein the first gene is under transcriptional control of a TRE chosen from: one or more iterations of an NF-κB TRE, a CREB TRE, a STAT1 TRE, a STAT3 TRE, a STAT 1/2 heterodimer TRE, an IRF1 TRE, an NFAT TRE, a FOXO1 TRE, an ETS1 TRE, an AP-1 TRE, an HIF-1 TRE, an ETS-1 TRE, or a RELA TRE, and optionally the microneedle array comprises a plurality of nucleic acids each independently under transcriptional control of a TRE chosen from: one or more iterations of an NF-κB TRE, a CREB TRE, a STAT1 TRE, a STAT3 TRE, a STAT 1/2 heterodimer TRE, an IRF1 TRE, an NFAT TRE, a FOXO1 TRE, an ETS1 TRE, an AP-1 TRE, an HIF-1 TRE, an ETS-1 TRE, or a RELA TRE.

28. Use of a microneedle array of any of clauses 1-18 to produce a biosensor tattoo for detection of an analyte in the skin of a patient.

29. A transgenic animal comprising a biosensor tattoo prepared according to any of clauses 19-27.

We claim:

1. A method of monitoring gene expression in a patient comprising:
   injecting at least a first nucleic acid at a site in the skin of a patient with a microneedle array produce a biosensor tattoo, the microneedle array comprising:
   a backing; and
   one or more microneedles attached to a side of the backing and comprising the first nucleic acid comprising a first gene encoding a colorimetric protein under transcriptional control of a vertebrate transcription factor-responsive element (TRE) such that when transfected into a vertebrate cell, the first gene is expressed differently in the presence of a vertebrate transcription factor that binds the TRE than in the absence of the transcription factor, and the difference in expression of the first gene is optically detectable; and
   detecting an expression level of at least the first gene by detecting a color intensity change at one or more addressable locations in the biosensor tattoo due to expression of the colorimetric protein of at least the first gene.

2. The method of claim 1, wherein the color intensity change is detected by imaging or scanning the biosensor tattoo and analyzing the image or scan by a computer method to detect any difference in color intensity of the skin at one or more wavelengths, at one or more addressable locations in the biosensor tattoo.

3. The method of claim 1, wherein the colorimetric protein is a fluorescent protein, and expression of at least the first gene is detected by illuminating the biosensor tattoo with light at an excitation wavelength of the colorimetric protein, and expression of the genes is detected by determining fluorescent intensity of the colorimetric protein at an emission wavelength of the colorimetric protein.

4. The method of claim 1, wherein the first gene is under transcriptional control of an NF-κB TRE, and wherein the expression levels of at least the first gene, as determined by imaging or scanning the biosensor tattoo, are related in a computer-implemented method to the patient's inflammation status.

5. The method of claim 2, wherein the imaging or scanning of the biosensor tattoo is performed by a device comprising:
   emitters that produce light at an excitation wavelength of the colorimetric proteins;
   an imaging sensor;
   a processor;
   data storage; and
   computer-implemented instructions implemented by the processor for storing image data obtained from the imaging sensor in the data storage.

6. The method of claim 5, in which the device is one or more of a smartphone, a smartwatch, a camera, a band, a strap, or another wearable device.

7. The method of claim 1, wherein the first gene is under transcriptional control of a TRE chosen from: AP-1 TRE, C/EBPalpha TRE, c-Fos TRE, c-Jun TRE, c-Myc TRE, c-Rel TRE, DP-1 TRE, E2F+p107 TRE, E2F-1 TRE, E2F-4/DP-2 TRE, Egr-1 TRE, ErbA TRE, FosB TRE, HIF-1 TRE, HSF1 TRE, INF TRE, JunD TRE, Max1 TRE, NF-κB TRE, N-Myc TRE, p53 TRE, REVERB-alpha TRE, Sp1 TRE, Sp3 TRE, SRF TRE, YY1 TRE, NFAT TRE, FOXO1 TRE, ETS-1 TRE, RELA TRE, STAT1 TRE, STAT2 TRE, STAT1/2 TRE, STAT3 TRE, CREB TRE, IRF1 TRE, and/or SRC-1 TRE, and optionally chosen from NF-KκTRE, a CREB TRE, a STAT1 TRE, a STAT3 TRE, a STAT 1/2 heterodimer TRE, an IRF1 TRE, an NFAT TRE, a FOXO1 TRE, an ETS1 TRE, an AP-1 TRE, an HIF-1 TRE, an ETS-1 TRE, or a RELA TRE.

8. The method of claim 1, wherein the microneedle array comprises at one or more additional discrete, addressable locations, independently, a nucleic acid comprising a second reporter gene encoding a colorimetric protein under transcriptional control of a TRE different from that of the first gene, the TRE chosen from one or more of AP-1 TRE, C/EBPalpha TRE, c-Fos TRE, c-Jun TRE, c-Myc TRE, c-Rel TRE, DP-1 TRE, E2F+p107 TRE, E2F-1 TRE, E2F-4/DP-2 TRE, Egr-1 TRE, ErbA TRE, FosB TRE, HIF-1 TRE, HSF1 TRE, INF TRE, JunD TRE, Max1 TRE, NF-κB TRE, N-Myc TRE, p53 TRE, REVERB-alpha TRE, Sp1 TRE, Sp3 TRE, SRF TRE, YY1 TRE, NFAT TRE, FOXO1 TRE, ETS-1 TRE, RELA TRE, STAT1 TRE, STAT2TRE, STAT1/2 TRE, STAT3 TRE, CREB TRE, IRF1 TRE, and/or SRC-1 TRE, and optionally from NF-κB TRE, a CREB TRE, a STAT1 TRE, a STAT3 TRE, a STAT 1/2 heterodimer TRE, an IRF1 TRE, an NFAT TRE, a FOXO1 TRE, an ETS1 TRE, an AP-1 TRE, an HIF-1 TRE, an ETS-1 TRE, or a RELA TRE.

9. The method of claim 3, wherein the fluorescent protein is a far-red or near-infrared fluorescent protein, and the far-red or near-infrared fluorescent protein is one of eqFP578, Katushka, mKate, mNeptune, e2-Crimson, TagRFP657, mCardinal, iRFP670, iRFP682, iRFP702, iRFP720, iSplit, PAiRFP1, PAiRFP2, mCherry, tdTomato, DsRed-Monomer, dsRed-Express2, dsRed-Express, dsRed2, asRed2, mStrawberry, mRuby, mApple, jRed, HcRed1, mRaspberry, dKeima-Tandem, mPlum, AQ143, mIFP, iFP1.4, iFP2.0, or NirFP.

10. The method of claim 1, wherein at least a portion of the one or more microneedles comprising the nucleic acids are dissolvable or bioerodible in vivo.

11. The method of claim 1, wherein at least the first nucleic acid is packaged in a viral transducing particle.

12. The method of claim 11, wherein the viral transducing particle is a herpes simplex virus, a gammaretrovirus, a lentivirus, or an Adeno-associated virus (AAV) transducing particle.

13. The method of claim 1, wherein the first gene is under transcriptional control of a transcription control sequence comprising a TRE including a minimal cytomegalovirus (CMV) promoter 3' to the TRE.

14. The method claim 11, wherein the viral transducing particle is an Adeno-associated virus (AAV) transducing particle comprising a self-complementary AAV genome.

15. The method of claim 5, wherein the device further comprises a wireless or wired communication module for transmitting data between the device and a computer.

16. The method of claim 5, wherein the device further comprises a display for providing output produced by the computer-implemented instructions.

17. The method of claim 5, wherein the device further comprises computer-implemented instructions capable of being implemented by the processor for analyzing the data to produce an output relating to expression levels of the at least first gene, transmitting data to and from the device, or outputting the image data or information produced by analysis of the image data.

* * * * *

UNITED STATES PATENT AND TRADEMARK OFFICE
CERTIFICATE OF CORRECTION

| | | |
|---|---|---|
| PATENT NO. | : 10,894,151 B2 | Page 1 of 1 |
| APPLICATION NO. | : 15/568327 | |
| DATED | : January 19, 2021 | |
| INVENTOR(S) | : O. Burak Ozdoganlar et al. | |

It is certified that error appears in the above-identified patent and that said Letters Patent is hereby corrected as shown below:

In the Specification

Column 1, Line 9, Delete "2016" and insert -- 2016, --

In the Claims

Column 53, Line 17, Claim 1, after "array" insert -- to --

Column 54, Line 25, Claim 7, delete "NF-KκTRE," and insert -- NF-κB TRE, --

Column 54, Line 42, Claim 8, delete "STAT2TRE," and insert -- STAT2 TRE, --

Column 54, Line 53, Claim 9, after "iRFP702," insert -- iRFP713 --

Column 55, Line 5, Claim 14, after "method" insert -- of --

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*